United States Patent
Zvuloni et al.

(10) Patent No.: US 7,399,298 B2
(45) Date of Patent: Jul. 15, 2008

(54) PLANNING AND FACILITATION SYSTEMS AND METHODS FOR CRYOSURGERY

(75) Inventors: Roni Zvuloni, Haifa (IL); Shaike Schatzberger, Haifa (IL)

(73) Assignee: Galil Medical Ltd., Yokneam (IL)

( * ) Notice: Subject to any disclaimer, the term of this patent is extended or adjusted under 35 U.S.C. 154(b) by 500 days.

(21) Appl. No.: 11/219,648

(22) Filed: Sep. 7, 2005

(65) Prior Publication Data
US 2006/0009751 A1 Jan. 12, 2006

Related U.S. Application Data

(60) Continuation of application No. 11/066,294, filed on Feb. 28, 2005, which is a division of application No. 09/917,811, filed on Jul. 31, 2001, now Pat. No. 6,905,492.

(60) Provisional application No. 60/221,891, filed on Jul. 31, 2000.

(51) Int. Cl.
*A61B 18/02* (2006.01)

(52) U.S. Cl. .......................................... 606/20; 128/898
(58) Field of Classification Search ............. 606/20–26; 128/898
See application file for complete search history.

(56) References Cited

U.S. PATENT DOCUMENTS

| | | |
|---|---|---|
| 5,391,199 A | 2/1995 | Ben-Haim |
| 5,412,619 A | 5/1995 | Bauer |
| 5,480,422 A | 1/1996 | Ben-Haim |
| 5,546,951 A | 8/1996 | Ben-Haim |
| 5,568,809 A | 10/1996 | Ben-Haim |
| 5,647,868 A | 7/1997 | Chinn |
| 5,694,945 A | 12/1997 | Ben-Haim |
| 5,706,810 A | 1/1998 | Rubinsky et al. |
| 5,713,946 A | 2/1998 | Ben-Haim |
| 5,718,241 A | 2/1998 | Ben-Haim et al. |
| 5,800,488 A | 9/1998 | Crockett |
| 5,840,025 A | 11/1998 | Ben-Haim |
| 5,954,665 A | 9/1999 | Ben-Haim |
| 6,063,022 A | 5/2000 | Ben-Haim |
| 6,083,170 A | 7/2000 | Ben-Haim |
| 6,142,991 A | 11/2000 | Schatzberger |
| 6,235,018 B1 | 5/2001 | LePivert |
| 6,256,529 B1 | 7/2001 | Holupka et al. |
| 6,419,690 B1 | 7/2002 | Mikus et al. |
| 6,477,426 B1 | 11/2002 | Fenn et al. |
| 6,905,492 B2 | 6/2005 | Zvuloni et al. |
| 2002/0040220 A1 | 4/2002 | Zvuloni et al. |
| 2005/0143723 A1 | 6/2005 | Zvuloni et al. |

*Primary Examiner*—Roy D. Gibson
*Assistant Examiner*—Pete J Vrettakos

(57) ABSTRACT

Systems and methods for planning a cryoablation procedure and for facilitating a cryoablation procedure utilize integrated images displaying, in a common virtual space, a three-dimensional model of a surgical intervention site based on digitized preparatory images of the site from first imaging modalities, simulation images of cryoprobes used according to an operator-planned cryoablation procedure at the site, and real-time images provided by second imaging modalities during cryoablation. The system supplies recommendations for and evaluations of the planned cryoablation procedure, feedback to an operator during cryoablation, and guidance and control signals for operating a cryosurgery tool during cryoablation. Methods are provided for generating a nearly-uniform cold field among a plurality of cryoprobes, for cryoablating a volume with smooth and well-defined borders, thereby minimizing damage to healthy tissues.

9 Claims, 17 Drawing Sheets

PLANNING AND FACILITATION SYSTEMS AND METHODS FOR CRYOSURGERY

RELATED APPLICATIONS

The present application is a Continuation of U.S. patent application Ser. No. 11/066,294, filed on Feb. 28, 2005, which is a Divisional of U.S. patent application Ser. No. 09/917,811, filed on Jul. 31, 2001, now U.S. Pat. No. 6,905,492, issued on Jun. 14, 2005, which claims priority from U.S. Provisional Patent Application No. 60/221,891, filed on Jul. 31, 2000. The contents of all of the above-mentioned applications are herein incorporated by reference.

FIELD AND BACKGROUND OF THE INVENTION

The present invention relates to cryosurgical systems and methods useable for planning and for facilitating a cryoablation procedure. More particularly, the present invention relates to the use of integrated images displaying, in a common virtual space, images of a three-dimensional model of a surgical intervention site, simulation images of a planned cryoablation procedure at the site, and real-time images of the site during cryoablation. The present invention further relates to system-supplied recommendations for, and evaluations of, a planned cryoablation procedure, and to system-supplied feedback to an operator and system-supplied control signals to a cryosurgery tool during cryoablation.

Cryosurgical procedures involve deep tissue freezing which results in tissue destruction due to rupture of cells and or cell organelles within the tissue. Deep tissue freezing is effected by insertion of a tip of a cryosurgical device into the tissue, either transperineally, endoscopically or laparoscopically, and a formation of, what is known in the art as, an ice-ball around the tip.

In order to effectively destroy a tissue by such an ice-ball, the diameter of the ball should be substantially larger than the region of the tissue to be treated, which constraint derives from the specific profile of temperature distribution across the ice-ball.

Specifically, the temperature required for effectively destroying a tissue is about $-40°$ C., or cooler. However, the temperature at the surface of the ice-ball is $0°$ C. The temperature declines exponentially towards the center of the ball such that an isothermal surface of about $-40°$ C. is typically located within the ice-ball substantially at the half way between the center of the ball and its surface.

Thus, in order to effectively destroy a tissue there is a need to locate the isothermal surface of $-40°$ C. at the periphery of the treated tissue, thereby exposing adjacent, usually healthy, tissues to the external portions of the ice-ball. The application of temperatures of between about $-40°$ C. and $0°$ C. to such healthy tissues usually causes substantial damage thereto, which damage may result in temporary or permanent impairment of functional organs.

In addition, when the adjacent tissues are present at opposite borders with respect to the freeze treated tissue, such as in the case of prostate freeze treatments, as is further detailed below, and since the growth of the ice-ball is in substantially similar rate in all directions toward its periphery, if the tip of the cryosurgical device is not precisely centered, the ice-ball reaches one of the borders before it reaches the other border, and decision making of whether to continue the process of freezing, risking a damage to close healthy tissues, or to halt the process of freezing, risking a non-complete destruction of the treated tissue, must be made.

Although the present invention is applicable to any cryosurgical treatment, discussion is hereinafter primarily focused on a cryosurgical treatment of a patient's prostate.

Thus, when treating a tumor located at a patient's prostate, there is a trade-of between two options: (a) effectively destroying the prostatic tissue extending between the prostatic urethra and the periphery of the prostate and causing unavoidable damage to the patient's urethra or organs adjacent the prostate such as the rectum and nerves; (b) avoiding the damaging of the prostatic urethra and adjacent organs, but exposing the patient to the risk of malignancy due to ineffective destruction of the prostate tumor. Treatment of benign prostate hyperplasia (BPH), while not requiring total destruction of an entire volume of prostate tissue as does treatment of a malignancy, nevertheless does run the risk of causing damage to healthy functional tissues and organs adjacent to the prostate, if care is not taken to limit the scope of destructive freezing to appropriate locations.

A classical cryosurgery procedure for treating the prostate includes the introduction of 5-7 probes into the prostate, the probes being typically arranged around the prostatic urethra such that a single probe is located, preferably centered, between the prostatic urethra and the periphery of the prostate. The dimensions of such a single-probe are usually adapted for effectively treating the prostatic tissue segment extending from the urethra to the periphery of the prostate, e.g., a tip of 3 millimeters in diameter, generating an ice-ball of 3-4 centimeters in diameter, depending on the size of the prostate. Since a single ice-ball is used for freezing such a prostatic tissue segment, the volume of adjacent tissues exposed to damage is substantially greater than the volume of the treated tissue. For example, if the area of the ice-ball in cross section is $\pi R^2$, and an effective treatment of at least $-40°$ C. is provided to an area of $\pi(R/2)^2$ (in cross section), then the area of adjacent tissues (in cross section) exposed to between about $-40°$ C. and about $0°$ C. is $\pi R^{2-0.25}(\pi R^2) = 0.75(\pi R^2)$, which is three times the area of the tissue effectively treated by the ice-ball.

A modification of the classic cryosurgery procedure described in the preceding paragraph, intended to avoid excessive damage to adjacent tissues, is to use such a single probe of a smaller diameter producing an ice-ball of smaller size. Such a modification, however, exposes the patient to the danger of malignancy because of a possible incomplete destruction of the tumor.

The classical cryosurgery procedure herein described, therefore, does not provide effective resolution of treatment along the planes perpendicular to the axis of penetration of the cryosurgical probe into the patient's organ.

A further limitation of the classical procedure stems from the fact that anatomical organs such as the prostate usually feature an asymmetric three-dimensional shape. Consequently, introduction of a cryosurgical probe along a specific path of penetration within the organ may provide effective treatment to specific regions located at specific depths of penetration but at the same time may severely damage other portions of the organ located at other depths of penetration.

U.S. Pat. No. 6,142,991 to Schatzberger teaches a high resolution cryosurgical method and device for treating a patient's prostate designed to overcome the described limitations of the classical cryosurgery procedure described hereinabove. Schatzberger's "high resolution" method (referred to as the "HR method" hereinbelow) comprises the steps of (a) introducing a plurality of cryosurgical probes to the prostate, the probes having a substantially small diameter and are distributed across the prostate, so as to form an outer arrangement of probes adjacent the periphery of the prostate and an inner arrangement of probes adjacent the prostatic urethra; and (b) producing an ice-ball at the end of each of said cryosurgical probes, so as to locally freeze a tissue segment of the prostate. Schatzberger's apparatus (referred to hereinbelow as the "HR" apparatus) comprises (a) a plurality of cryosurgical probes of small diameter, the probes serve for insertion into the patient's organ, the probes being for producing ice-balls for locally freezing selected portions of the organ; (b) a guiding element including a net of apertures for inserting the cryosurgical probes therethrough; and (c) an imaging device for providing a set of images, the images being for providing information on specific planes located at specific depths within the organ, each of said images including a net of marks being correlated to the net of apertures of the guiding element, wherein the marks represent the locations of ice-balls which may be formed by the cryosurgical probes when introduced through said apertures of the guiding element to said distinct depths within the organ.

The HR method and device provide the advantages of high resolution of treatment along the axis of penetration of the cryosurgical probe into the patient's organ as well as along the planes perpendicular to the axis of penetration, thereby enabling to effectively destroy selective portions of a patient's tissue while minimizing damage to adjacent tissues and organs, and to selectively treat various portions of the tissue located at different depths of the organ, thereby effectively freezing selected portions of the tissue while avoiding the damaging of other tissues and organs located at other depth along the axis of penetration.

Schatzberger, in U.S. Pat. No. 6,142,991 also teaches the additional step of three dimensionally mapping an organ of a patient so as to form a three dimensional grid thereof, and applying a multi-probe system introduced into the organ according to the grid, so as to enable systematic high-resolution three dimensional cryosurgical treatment of the organ and selective destruction of the treated tissue with minimal damage to surrounding, healthy, tissues.

It is, however, a disadvantage of the HR apparatus and method as taught in U.S. Pat. No. 6,142,991 that the apparatus enables, and the method requires, a high level of diagnostic sophistication in the selection and definition of the particular volume of tissue to be cryoablated. Real-time imaging capabilities of the HR apparatus provide for imaging of the target organ at a selected depth of penetration and thereby assist an operator in deciding where to introduce and utilize a plurality of cryogenic probes, yet the complex three-dimensional geometry of the cryoablation target is poorly rendered by the set of two dimensional images constituting the three dimensional grid as contemplated by the HR method and apparatus. In this prior art method, little assistance is provided for an operator in understanding the three dimensional shape and structure of the cryoablation target and the surrounding tissues. Information vital to the operator may be present in the set of images, yet difficult for the operator to see and appreciate. In a set of images of this type, the details may be present, yet it may be difficult to appreciate their significance because of the difficulty of seeing them in context. A three dimensional "grid" composed of a plurality of two dimensional images such as ultrasound images contain many details, yet do not facilitate the understanding of those details in a three dimensional context.

Thus there is a widely recognized need for, and it would be highly advantageous to have, an apparatus for facilitating cryosurgery which provides real-time imaging of a cryoablation target site in a manner which is easy for an operator to visualize and to understand.

It is an additional limitation of the HR method and apparatus, and of other prior art systems, that the imaging capabilities contemplated are not well adapted to assist an operator in planning a cryoablation procedure. In addition to the fact that the imaging facilities there provided are poorly adapted to visualization of the three dimensional space by an operator, they are also limited in that the apparatus is poorly adapted to providing images of the target area in advance of the operation, e.g., for planning purposes. The described HR equipment might, of course, but used to create the described three dimensional mapping of the target area well in advance of a surgical intervention, but no mechanism is provided for facilitating the relating the images so obtained, and any planned procedures based on those images, to a subsequent intervention procedure. Moreover, the fact that the imaging modality of the HR apparatus is physically connected to parts of the cryosurgery equipment limits its versatility and may in some cases make it awkward to use for creating preparatory images of an intervention site.

Thus there is a widely recognized need for, and it would be highly advantageous to have, an apparatus for planning and for facilitating cryosurgery which provides easily understandable visualization of a cryoablation target site in advance of a surgical intervention, which further provides facilities for studying the site and for planning the intervention, and which yet further provides facilities for applying information gleaned from prior study of the imaged site, and specific plans for intervening in the site, to the actual site, in real time, during the planned cryoablation operation.

It is a further limitation of the HR method that no means are provided for facilitating the relating of images obtained in advance of a surgical intervention to a subsequent intervention. Yet whereas ultrasound images of a target site can be generated in real time during an intervention, and MRI techniques may also (if somewhat less easily) also be obtained during cryosurgery, other imaging techniques (CT scans, for example) are less well adapted to being produced during the course of an actual cryosurgery intervention.

Thus there is a widely recognized need for, and it would be highly advantageous to have, an apparatus and method for facilitating the relating of images obtained prior surgery to real-time images, from the same or from additional sources, obtained during cryosurgery.

Much is now known about the tissue-destructive processes of cryoablation, and about the subsequent short-term and long-term consequences to an organ such as a prostate which has undergone partial cryoablation. The laws of physics relating to the conduction of heat in a body, reinforced by experimentation and further reinforced by accumulated clinical experience in cryosurgery, provide a wealth of information enabling to predict with some accuracy the effect of a specific planned cryoablation procedure on target tissues. This information, and this capability for prediction, is underutilized in current cryosurgery practice.

The Seednet Training And Planning Software ("STPS") marketed by Galil Medical Ltd. of Yokneam, Israel constitutes a set in this direction, in that it provides a system for displaying, and allowing an operator to manipulate, a three-dimensional model of a prostate, and further allows an operator to plan a cryoablation intervention and to visualize the predicted effect of that planned intervention on the prostate tissues. STPS, however, is limited in that it does not provide means for relating a preliminary three dimensional model of a prostate to the prostate as revealed in real-time during the course of a surgical procedure. Moreover, the predictive ability of the STPS system is limited to predicting the extent of the freezing produced by a given deployment of a plurality of cryoprobes over a given time. No assistance is provided to an operator in discerning interactions between the predicted cryoablation and specific structures desired to be protected or to be destroyed. No assistance is given in predicting long-term effects of a given cryoablation procedure. No assistance is given in recommending procedures, placement of probes, temperature, or timing of an intervention.

Thus there is a widely recognized need for, and it would be highly advantageous to have, apparatus and method for calculating probable immediate, short-term, and long-term effects of a planned cryoablation procedure, thereby to facilitate the planning of such a procedure. There is further a widely recognized need for, and it would be highly advantageous to have, apparatus and method for facilitating the implementation of such a planned procedure, in real time, during execution of a planned cryoablation.

It is noted that with respect to BPH, the need for such a planning and facilitation apparatus is particularly strong.

BPH, which affects a large number of adult men, is a non-cancerous enlargement of the prostate. BPH frequently results in a gradual squeezing of the portion of the urethra which traverses the prostate, also known as the prostatic urethra. This causes patients to experience a frequent urge to urinate because of incomplete emptying of the bladder and a burning sensation or similar discomfort during urination. The obstruction of urinary flow can also lead to a general lack of control over urination, including difficulty initiating urination when desired, as well as difficulty in preventing urinary flow because of the residual volume of urine in the bladder, a condition known as urinary incontinence. Left untreated, the obstruction caused by BPH can lead to acute urinary retention (complete inability to urinate), serious urinary tract infections and permanent bladder and kidney damage.

Most males will eventually suffer from BPH. The incidence of BPH for men in their fifties is approximately 50% and rises to approximately 80% by the age of 80. The general aging of the United States population, as well as increasing life expectancies, is anticipated to contribute to the continued growth in the number of BPH sufferers.

Patients diagnosed with BPH generally have several options for treatment: watchful waiting, drug therapy, surgical intervention, including transurethral resection of the prostate (TURP), laser assisted prostatectomy and new less invasive thermal therapies.

Various disadvantages of existing therapies have limited the number of patients suffering from BPH who are actually treated. In 1999, the number of patients actually treated by surgical approaches was estimated to be 2% to 3%. Treatment is generally reserved for patients with intolerable symptoms or those with significant potential symptoms if treatment is withheld. A large number of the BPH patients delay discussing their symptoms or elect "watchful waiting" to see if the condition remains tolerable.

Thus, development of a less invasive, more convenient, or more successful treatment for BPH could result in a substantial increase in the number of BPH patients who elect to receive interventional therapy.

Cryoablation is a candidate for being such a popularize treatment.

With respect to drug therapies: some drugs are designed to shrink the prostate by inhibiting or slowing the growth of prostate cells. Other drugs are designed to relax the muscles in the prostate and bladder neck to relieve urethral obstruction. Current drug therapy generally requires daily administration for the duration of the patient's life.

With respect to surgical interventions: the most common surgical procedure, transurethral resection of the prostate (TURP), involves the removal of the prostate's core in order to reduce pressure on the urethra. TURP is performed by introducing an electrosurgical cutting loop through a cystoscope into the urethra and "chipping out" both the prostatic urethra and surrounding prostate tissue up to the surgical capsule, thereby completely clearing the obstruction. It will be appreciated that this procedure results in a substantial damage inflicted upon the prostatic urethra.

With respect to laser ablation of the prostate: laser assisted prostatectomy includes two similar procedures, visual laser ablation of the prostate (V-LAP) and contact laser ablation of the prostate (C-LAP), in which a laser fiber catheter is guided through a cystoscope and used to ablate and coagulate the prostatic urethra and prostatic tissue. Typically, the procedure is performed in the hospital under either general or spinal anesthesia, and an overnight hospital stay is required. In V-LAP, the burnt prostatic tissue then necroses, or dies and over four to twelve weeks is sloughed off during urination. In C-LAP, the prostatic and urethral tissue is burned on contact and vaporized. Again, it will be appreciated that these procedures result in a substantial damage inflicted upon the prostatic urethra.

With respect to heat ablation therapies: these therapies, under development or practice, are non-surgical, catheter based therapies that use thermal energy to preferentially heat diseased areas of the prostate to a temperature sufficient to cause cell death. Thermal energy forms being utilized include microwave, radio frequency (RF) and high frequency ultrasound energy (HIFU). Both microwave and RF therapy systems are currently being marketed worldwide. Heat ablation techniques, however, burn the tissue, causing irreversible damage to peripheral tissue due to protein denaturation, and destruction of nerves and blood vessels. Furthermore, heat generation causes secretion of substances from the tissue which may endanger the surrounding area.

With respect to transurethral RF therapy: transurethral needle ablation (TUNA) heats and destroys enlarged prostate tissue by sending radio waves through needles urethrally positioned in the prostate gland. The procedures prolongs about 35 to 45 minutes and may be performed as an outpatient procedure. However TUNA is less effective than traditional surgery in reducing symptoms and improving urine flow. TUNA also burn the tissue, causing irreversible damage to peripheral tissue due to protein denaturation, and destruction of nerves and blood vessels. Furthermore, as already discussed above, heat generation causes secretion of substances from the tissue which may endanger the surrounding area.

In contrast to the alternative treatments for BPH listed above, cryoablation therapy presents significant advantages. The volume of an enlarged prostate can be reduced, and stricture to the urethra can be eliminated, by selective destruction of prostate tissue by cryoablation. Tissues destroyed by cryoablation in treating BPH are gradually absorbed by the body, rather than being sloughed off during urination.

When the tissues to be cryoablated are appropriately selected and accurately cryoablated, there may be minimal endangerment of vital healthy functional tissues in proximity to the prostate. Thus, cryoablation is an important technique for treating BPH and has potential for becoming an increasingly popular therapy and enabling treatment of a large population of sufferers who today receive no effective treatment at all for their condition.

Thus, there is a widely recognized need for, and it would be highly advantageous to have, apparatus and method facilitating the planning cryoablation for the treatment of BPH by recommending appropriate number or placement of loci for cryoablation based on a patient's symptomatology, thereby helping to make this useful therapy accessible to surgeons not specialized in this specific method of treatment.

Particularly for surgeons who are not specialists in the particular limited field of cryoablation of the prostate, there is a widely recognized need for, and it would be highly advantageous to have, apparatus and method which facilitates the execution of a planned cryoablation treatment of the prostate or of another organ by providing feedback on the progress of an intervention by comparing real-time imaging of the intervention site with a planning model of the site, providing warnings when freezing, visible in ultrasound, approaches areas designated as needing to be protected from damage, or when destruction of tissues risks failing to cover volumes designated as requiring to be destroyed. Similarly, there is a widely recognized need for, and it would be highly advantageous to have, mechanisms for guiding movements of an operator during a cryoablation procedure, or for automatically managing the movement of cryosurgical tools such as cryoprobes during a cryoablation intervention, according to information based on a plan of the intervention and feedback obtained through real-time imaging of the intervention site.

In one respect, a system for planning a cryoablation intervention is particularly useful. Prior art has given little consideration to the interactive effects of a plurality of closely placed cryoprobes. Yet tissues which are in proximity to two or more cryoprobes may be cooled by several sources simultaneously, and consequently achieve a lower temperature than would be expected when considering the well-known freezing patterns created by a single cryoprobe used in isolation.

Thus there is a widely recognized need for, and it would be highly advantageous to have, system and method for utilizing a plurality of cryoprobes that takes into account their mutually-reinforcing cooling effect to create a near-uniform cold field within a volume. It would further be advantageous to have a system and method for defining a volume in which cognizance is take of the mutually reinforcing cooling effect of a plurality of closely placed cryoprobes to smoothly and accurately define a border of a cryoablation volume, thereby ensuring total destruction of tissues within that volume while minimizing damage to tissues outside that volume.

SUMMARY OF THE INVENTION

According to one aspect of the present invention there is provided a planning system for planning a cryosurgical ablation procedure, comprising a first imaging modality for creating digitized preparatory images of an intervention site, a three-dimensional modeler for creating a three-dimensional model of the intervention site based on the digitized preparatory images; and a simulator for simulating a cryosurgical intervention, having an interface useable by an operator for specifying loci for insertion of cryoprobes and operational parameters for operation of the cryoprobes for cryoablating tissues, and a displayer for displaying in a common virtual space an integrated image comprising a display of said three-dimensional model of said intervention site and a virtual display of cryoprobes inserted at said loci.

According to further features in preferred embodiments of the invention described below, the planning system further comprises a memory for storing said specified loci for insertion of cryoprobes and said operational parameters for operation of said cryoprobes.

According to still further features in the described preferred embodiments the first imaging modality is selected from the group consisting of magnetic resonance imaging, ultrasound imaging and computerized tomography imaging, and the three-dimensional model is expressible in a three-dimensional Cartesian coordinate system.

According to still further features in the described preferred embodiments the interface also serves for highlighting selected regions within the three-dimensional model, and the integrated image further comprises a display of an operator-highlighted regions. The interface is useable by an operator for identifying tissues to be cryoablated and for identifying tissues to be protected from damage during cryoablation, and the integrated image further comprises a display of said operator-identified tissues to be cryoablated and of said operator-identified tissues to be protected from damage during said cryoablation.

According to still further features in the described preferred embodiments the system further comprises a predictor for predicting an effect on tissues of the patient of operation of the cryoprobes at the loci according to the operational parameters, and the model displayer additionally displays in the common virtual space a representation of the predicted effect.

According to still further features in the described preferred embodiments, the system further comprises an evaluator for comparing the predicted effect to an operator-defined goal of the procedure. The evaluator is for identifying areas of predicted less-than-total destruction of tissues within a volume of desired total destruction of tissues as defined by an operator, and for identifying areas specified as requiring protection during cryoablation which may be endangered by a specified planned cryoablation procedure.

According to still further features in the described preferred embodiments, the system comprises a recommender for recommending cryosurgical procedures to an operator, the recommendation being based on goals of a cryoablation procedure, the goals being specified by an operator, and further being based on the three-dimensional model of the site, thereby facilitating planning the cryoablation procedure. The recommender may recommend an optimal number of cryoprobes for use in a cryoablation procedure, or an optimal temperature for a cryoprobe for use in a cryoablation procedure, or an optimal duration of cooling for a cryoprobe for use in a cryoablation procedure. The recommendation may be based on a table of optimal interventions based on expert recommendations, or on a table of optimal interventions based on compiled feedback from a plurality of operators, and may comprise specific locations for insertion of a cryoprobe to affect cryoablation. The recommended procedures may be for cryoablation of tissues of a prostate, for treating BPH percutaneously or transperineally, or for treating a mass or a malignancy. The table may comprise a measure of volume of a prostate, or a measure of length of a stricture of a urethra or a measure of symptomatic severity of a BPH condition such as an AUA questionnaire score.

The recommendation may be of multiple cryoprobes closely placed so as to ensure a continuous cold field sufficient to ensure complete destruction of tissues within a target volume, while minimizing damage to tissues outside said target volume.

According to another aspect of the present invention there is provided a surgical facilitation system for facilitating a cryosurgery ablation procedure, comprising a first imaging modality, for creating digitized preparatory images of an intervention site, a three-dimensional modeler for creating a first three-dimensional model of the intervention site based on the digitized preparatory images, a second imaging modality, for creating a digitized real-time image of at least a portion of the intervention site during a cryosurgery procedure, and an images integrator for integrating information from the three-dimensional model of the site and from the real-time image of the site in a common coordinate system, thereby producing an integrated image.

According to further features in preferred embodiments of the invention described below, the surgical facilitation system further comprising a planning system as described hereinabove.

According to still further features in the described preferred embodiments the surgical facilitation system further comprises a displayer for displaying the integrated image in a common virtual space. The displayed integrated image may be a two-dimensional image or a three-dimensional image.

According to still further features in the described preferred embodiments the surgical facilitation system further comprises a three-dimensional modeler for creating a second three-dimensional model of at least a portion of the intervention site based on a plurality of real-time images. The images integrator may be operable for integrating information from the first three-dimensional model of the site and from the second three-dimensional model of at least a portion of the site in a common coordinate system.

According to still further features in the described preferred embodiments the first imaging modality comprises at least one of a group comprising magnetic resonance imaging, ultrasound imaging, and computerized tomography imaging, and the second imaging modality comprises at least one of a group comprising magnetic resonance imaging, ultrasound imaging, and computerized tomography imaging.

According to still further features in the described preferred embodiments the second imaging modality comprises an imaging tool operable to report a position of the tool during creation of the real-time image, thereby providing localizing information about the real-time image useable by the images integrator.

According to still further features in the described preferred embodiments the imaging tool is an ultrasound probe inserted in the rectum of a patient and operable to report a distance of penetration in the rectum of the patient during creation of ultrasound images of a prostate of the patient.

According to still further features in the described preferred embodiments the first three-dimensional model is expressed in a three-dimensional Cartesian coordinate system.

According to still further features in the described preferred embodiments the surgical facilitation system further comprises an interface useable by an operator for highlighting selected regions within the first three-dimensional model and the integrated image further comprises a display of an operator-highlighted region. The interface is useable by an operator for identifying tissues to be cryoablated or for identifying tissues to be protected from damage during cryoablation, and integrated image further comprises a display of operator-identified tissues to be cryoablated or of operator-identified tissues to be protected from damage during said cryoablation. The interface is also useable by an operator for labeling topographic features of the first three-dimensional model and of the real-time images or of the second three-dimensional model.

According to still further features in the described preferred embodiments the images integrator matches operator-labeled topographic features of the first three-dimensional model with operator-labeled features of the real-time images, to orient the first three-dimensional model and the real-time image with respect to the common coordinate system.

According to still further features in the described preferred embodiments the images integrator matches operator-labeled topographic features of the first three-dimensional model with operator-labeled features of the second three-dimensional model, to orient the first three-dimensional model and second three-dimensional model with respect to a common coordinate system.

According to still further features in the described preferred embodiments comprises a simulator for simulating a cryosurgical intervention, the simulator comprising an interface useable by an operator during a planning phase of the intervention, for specifying loci for insertion of cryoprobes and operational parameters for operation of the cryoprobes for cryoablating tissues, the image integrator being operable to integrate the operator-specified loci for insertion of cryoprobes into the integrated image, and the displayer being operable to display the integrated image.

According to still further features in the described preferred embodiments the surgical facilitation system further comprises a first comparator for comparing the first three-dimensional model with the real-time image to determine differences, a representation of the differences being further displayed by the displayer in the integrated image.

According to still further features in the described preferred embodiments the surgical facilitation system further comprises apparatus for providing feedback to an operator regarding position of tools being used during a surgical intervention as compared to the loci for insertion of cryoprobes specified by an operator during the planning phase of the intervention. The system further comprises apparatus for providing feedback to an operator regarding position of tools being used during a surgical intervention as compared to operator-identified tissues to be cryoablated, and apparatus for providing feedback to an operator regarding position of tools being used during a surgical intervention as compared to operator-identified tissues to be protected during cryoablation, and apparatus for guiding an operator in the placement of cryoprobes for affecting cryoablation, the guiding being according to the loci for insertion of cryoprobes specified by an operating during the planning phase of the intervention.

According to still further features in the described preferred embodiments the surgical facilitation system further comprises apparatus for limiting movement of a cryoprobes during a cryoablation intervention, the limitation being according to the loci for insertion of cryoprobes specified by an operating during the planning phase of the intervention.

According to still further features in the described preferred embodiments the surgical facilitation system further comprises a cryoprobe displacement apparatus for moving at least one cryoprobe to at least one of the loci for insertion of cryoprobes specified by an operating during the planning phase of the intervention.

According to still further features in the described preferred embodiments the cryoprobe displacement apparatus comprises a stepper motor and a position sensor, and the surgical facilitation system is operable to affect cooling of the at least one cryoprobe, heating of at least one cryoprobe, and is operable to affect scheduled movement of at least one cryoprobe coordinated with scheduled alternative heating and cooling of at least one cryoprobe, to affect cryoablation at a plurality of loci.

According to yet another aspect of the present invention there is provided a cryoablation method for ensuring complete destruction of tissues within a selected target volume while minimizing destruction of tissues outside the selected target volume, comprising deploying a plurality of cryoprobes in a dense array within the target volume, and cooling the cryoprobes to affect cryoablation, while limiting the cooling to a temperature only slightly below a temperature ensuring complete destruction of tissues, thereby limiting destructive range of each cooled cryoprobe, the plurality of cryoprobes being deployed in an array sufficiently dense to ensure destruction of tissues within the target volume.

According to still further features in the described preferred embodiments the method further comprises a planner for planning the dense array, the planner utilizing a three-dimensional model of the target volume to calculate a required density of the dense array of deployed cryoprobes operated at a selected temperature, to affect complete destruction of tissues within the selected target volume.

According to still further features in the described preferred embodiments the method further comprises using a planner for planning the dense array, the planner utilizing a three-dimensional model of the target volume to calculate, for a plurality of cryoprobes deployed to a selected array of freezing loci, a temperature and duration of cooling for each of the cryoprobes sufficient to affect complete destruction of tissues within the selected target volume, while also minimizing cooling of tissues outside of the selected target volume.

According to yet another aspect of the present invention there is provided a cryoablation method ensuring complete destruction of tissues within a selected target volume while minimizing destruction of tissues outside the selected target volume, comprising utilizing cryoprobes to affect cryoablation at a plurality of freezing loci, the loci being of a first type and of a second type, the first type being located adjacent to a surface of the selected target volume and the second type being located at an interior portion of the selected target volume, and cooling cryoprobes deployed at loci of the first type to a first degree of cooling and cooling cryoprobes deployed at loci of the second type to a second degree of cooling, the first degree of cooling being less cooling than the second degree of cooling, thereby affecting wide areas of destruction around each cryoprobe deployed at loci of the second type and narrow areas of destruction around each cryoprobe deployed at loci of the first type, thereby ensuring complete destruction of tissues within a selected target volume while minimizing destruction of tissues outside the selected target volume.

According to still further features in the described preferred embodiments cryoprobes deployed to freezing loci of the first type are cooled to a first temperature and cryoprobes deployed to freezing loci of the second type are cooled to a second temperature, the second temperature being lower than the first temperature.

According to still further features in the described preferred embodiments cryoprobes deployed to freezing loci of the first type are cooled for a first length of time, and cryoprobes deployed to freezing loci of the second type are cooled for a second length of time, the second length of time being longer than the first length of time.

According to still further features in the described preferred embodiments the method further comprises a planner for planning the dense array, the planner utilizing a three-dimensional model of the target volume to calculate, for a given array of freezing loci, a required temperature and length of cooling time for loci of the first type and for loci of the second type, to affect complete destruction of tissues within the selected target volume while minimizing destruction of issues outside the selected target volume.

According to yet another aspect of the present invention there is provided a method for planning a cryosurgical ablation procedure, comprising utilizing a first imaging modality to create digitized preparatory images of an intervention site, utilizing a three-dimensional modeler to create a three-dimensional model of the intervention site based on the digitized preparatory images, and utilizing a simulator having an interface useable by an operator for specifying loci for insertion of cryoprobes and for specifying operational parameters for operation of the cryoprobes, to specify loci for insertion of cryoprobes and operational parameters for operation of the cryoprobes for cryoablating tissues, thereby simulating a planned cryosurgical ablation procedure.

According to still further features in the described preferred embodiments, the method further comprises utilizing a displayer to display in a common virtual space an integrated image comprising a display of the three-dimensional model of the intervention site and a virtual display of cryoprobes inserted at the loci, and utilizing a memory to store the specified loci for insertion of cryoprobes and the operational parameters for operation of the cryoprobes. The first imaging modality is selected from the group consisting of magnetic resonance imaging, ultrasound imaging and computerized tomography imaging. The three-dimensional model is expressible in a three-dimensional Cartesian coordinate system. The method further comprises utilizing the interface to highlight selected regions within the three-dimensional model. Highlighting maybe be used to identify tissues to be cryoablated and to identify tissues to be protected from damage during cryoablation.

According to still further features in the described preferred embodiments the method further comprises utilizing a predictor to predict an effect on tissues of the patient of operation of the cryoprobes at the loci according to the operational parameters, and the model displayer additionally displays in the common virtual space a representation of the predicted effect.

According to still further features in the described preferred embodiments the method further comprises utilizing an evaluator to compare the predicted effect to an operator-defined goal of the procedure.

According to still further features in the described preferred embodiments the method further comprising utilizing the evaluator to identify areas of predicted less-than-total destruction of tissues within a volume of desired total destruction of tissues as defined by an operator, and utilizing the evaluator to identify areas specified as requiring protection during cryoablation which may be endangered by a specified planned cryoablation procedure.

According to still further features in the described preferred embodiments the method further comprises utilizing a recommender for recommending cryosurgical procedures, the recommendation being based on goals of a cryoablation procedure, the goals being specified by an operator, and further being based on the three-dimensional model of the site. The recommender recommends an optimal number of cryoprobes for use in a cryoablation procedure, an optimal temperature for a cryoprobe for use in a cryoablation procedure, an optimal duration of cooling for a cryoprobe for use in a cryoablation procedure. The recommendation is based on a table of optimal interventions based on expert recommendations, or on a table of optimal interventions based on compiled feedback from a plurality of operators.

According to still further features in the described preferred embodiments the recommendation comprises specific locations for insertion of a cryoprobe to affect cryoablation.

According to still further features in the described preferred embodiments the recommended procedures are for cryoablation of tissues of a prostate.

According to still further features in the described preferred embodiments the recommended procedures are for treating BPH, percutaneously or transperineally.

According to still further features in the described preferred embodiments the recommended procedures are for treating a mass.

According to still further features in the described preferred embodiments the recommended procedures are for treating a malignancy.

According to still further features in the described preferred embodiments the table comprises a measure of volume of a prostate.

According to still further features in the described preferred embodiments the table comprises a measure of length of a stricture of a urethra.

According to still further features in the described preferred embodiments the table comprises a measure of symptomatic severity of a BPH condition.

According to still further features in the described preferred embodiments the measure of symptomatic severity of a BPH condition is an AUA score.

According to still further features in the described preferred embodiments the recommendation is of multiple cryoprobes closely placed so as to ensure a continuous cold field sufficient to ensure complete destruction of tissues within a target volume, while minimizing damage to tissues outside the target volume.

According to still another aspect of the present invention there is provided a method for facilitating a cryosurgery ablation procedure, comprising utilizing a first imaging modality for creating digitized preparatory images of an intervention site, utilizing a three-dimensional modeler for creating a first three-dimensional model of the intervention site based on the digitized preparatory images, utilizing a second imaging modality for creating a digitized real-time image of at least a portion of the intervention site during a cryosurgery procedure, and utilizing an images integrator for integrating information from the three-dimensional model of the site and from the real-time image of the site in a common coordinate system, thereby producing an integrated image the site, facilitative to an operator practicing a cryoablation procedure.

According to still further features in the described preferred embodiments the method further comprises utilizing a planning method.

According to still further features in the described preferred embodiments the method further comprises utilizing a displayer for displaying the integrated image in a common virtual space.

According to still further features in the described preferred embodiments the displayed integrated image is a two-dimensional image.

According to still further features in the described preferred embodiments the displayed integrated image is a three-dimensional image.

According to still further features in the described preferred embodiments the method further comprises utilizing a three-dimensional modeler for creating a second three-dimensional model of at least a portion of the intervention site based on a plurality of real-time images.

According to still further features in the described preferred embodiments he method further comprises utilizing the images integrator to integrate information from the first three-dimensional model of the site and from the second three-dimensional model of at least a portion of the site in a common coordinate system.

According to still further features in the described preferred embodiments the first imaging modality comprises at least one of a group comprising magnetic resonance imaging, ultrasound imaging, and computerized tomography imaging.

According to still further features in the described preferred embodiments the second imaging modality comprises at least one of a group comprising magnetic resonance imaging, ultrasound imaging, and computerized tomography imaging.

According to still further features in the described preferred embodiments the method further comprises utilizing an imaging tool to report a position of the tool during creation of the real-time image, thereby providing localizing information about the real-time image useable by the images integrator.

According to still further features in the described preferred embodiments the imaging tool is an ultrasound probe inserted in the rectum of a patient operated to report a distance of penetration of the tool in the rectum of the patient during creation of ultrasound images of a prostate of the patient.

According to still further features in the described preferred embodiments the first three-dimensional model is expressed in a three-dimensional Cartesian coordinate system.

According to still further features in the described preferred embodiments the method further comprises utilizing an interface to highlight selected regions within the first three-dimensional model.

According to still further features in the described preferred embodiments the integrated image comprises a display of an operator-highlighted region.

According to still further features in the described preferred embodiments the method further comprises utilizing the interface for identifying tissues to be cryoablated.

According to still further features in the described preferred embodiments the integrated image further comprises a display of the operator-identified tissues to be cryoablated.

According to still further features in the described preferred embodiments he method further comprises utilizing the interface for identifying tissues to be protected from damage during cryoablation.

According to still further features in the described preferred embodiments the integrated image further comprises a display of the operator-identified tissues to be protected from damage during the cryoablation.

According to still further features in the described preferred embodiments the method further comprises utilizing the interface for labeling topographic features of the first three-dimensional model.

According to still further features in the described preferred embodiments the method further comprises utilizing the interface for labeling topographic features of the real-time images.

According to still further features in the described preferred embodiments the method further comprises utilizing the interface for labeling topographic features of the second three-dimensional model.

According to still further features in the described preferred embodiments the images integrator matches operator-labeled topographic features of the first three-dimensional model with operator-labeled features of the real-time images, to orient the first three-dimensional model and the real-time image with respect to the common coordinate system.

According to still further features in the described preferred embodiments the images integrator matches operator-labeled topographic features of the first three-dimensional model with operator-labeled features of the second three-dimensional model, to orient the first three-dimensional model and second three-dimensional model with respect to the common coordinate system.

According to still further features in the described preferred embodiments the method further comprises simulating a cryosurgical intervention by utilizing a simulator having an interface, and utilizing the interface during a planning phase of the intervention to specify loci for insertion of cryoprobes into a cryoablation site in a patient and to specify operational parameters for operation of the cryoprobes for cryoablating tissues, and further utilizing the image integrator to integrate the specified loci into the integrated image, and utilizing the displayer to display the integrated image.

According to still further features in the described preferred embodiments the method further comprises simulating a cryosurgical intervention by receiving from an operator during a planning phase of the intervention specifications of loci for insertion of cryoprobes into a cryoablation site and operational parameters for operation of the cryoprobes for cryoablating tissues, utilizing the image integrator to integrate the operator-specified loci into the integrated image, and utilizing the displayer to display the integrated image.

According to still further features in the described preferred embodiments the method further comprises utilizing a first comparator for comparing the first three-dimensional model with the real-time image to determine differences.

According to still further features in the described preferred embodiments the method further comprises utilizing apparatus for providing feedback to an operator regarding position of tools being used during a surgical intervention as compared to the loci for insertion of cryoprobes specified by an operator during the planning phase of the intervention.

According to still further features in the described preferred embodiments the method further comprises providing feedback to an operator regarding a position of a tool being used during a surgical intervention as compared to the loci for insertion of cryoprobes specified by an operator during the planning phase of the intervention.

According to still further features in the described preferred embodiments the method further comprises utilizing apparatus for providing feedback to an operator regarding a position of a tool being used during a surgical intervention as compared to a position of operator-identified tissues to be cryoablated.

According to still further features in the described preferred embodiments the method further comprises utilizing apparatus for providing feedback to an operator regarding a position of a tool being used during a surgical intervention as compared to a position of operator-identified tissues to be protected during cryoablation.

According to still further features in the described preferred embodiments the method further comprises utilizing apparatus for guiding an operator in the placement of cryoprobes for affecting cryoablation, the guiding being according to the loci for insertion of cryoprobes specified by an operating during the planning phase of the intervention.

According to still further features in the described preferred embodiments the method further comprises guiding an operator in the placement of cryoprobes for affecting cryoablation, the guiding being according to the loci for insertion of cryoprobes specified by an operating during the planning phase of the intervention.

According to still further features in the described preferred embodiments the method further comprises utilizing apparatus for limiting movement of a cryoprobe during a cryoablation intervention, the limitation being according to the loci for insertion of cryoprobes specified by an operating during the planning phase of the intervention.

According to still further features in the described preferred embodiments the method further comprises utilizing cryoprobe displacement apparatus for moving at least one cryoprobe to at least one of the loci for insertion of cryoprobes specified by an operator during the planning phase of the intervention.

According to still further features in the described preferred embodiments the method further comprises utilizing a stepper motor to move the cryoprobe.

According to still further features in the described preferred embodiments the method further comprises utilizing a position sensor to sense a position of the cryoprobe.

According to still further features in the described preferred embodiments the method further comprises utilizing control apparatus to control cooling of the at least one cryoprobe.

According to still further features in the described preferred embodiments the method further comprises utilizing control apparatus to control heating of the at least one cryoprobe.

According to still further features in the described preferred embodiments the method further comprises controlling the at least one cryoprobe according to a schedule of movements coordinated with a schedule of alternative heating and cooling of the at least one cryoprobe, to affect cryoablation at a plurality of loci.

The present invention successfully addresses the shortcomings of the presently known configurations by providing a system and method for effectively planning a cryoablation procedure by simulating such a procedure based on preparatory imaging of a target site in a patient, by simulating the procedure, by recommending procedural steps and by evaluating procedural steps specified by a user.

The present invention further successfully addresses the shortcomings of the presently known configurations by providing a system and method for facilitating a cryoablation intervention by relating preparatory imaging of a site, and plans for intervening at that site, to real-time images of the site during cryoablation.

The present invention further successfully addresses the shortcomings of the presently known configurations by providing a system and method for completely destroying target tissues at a cryoablation site while limiting damage to healthy tissues in close proximity to that site.

Implementation of the method and the apparatus of the present invention involves performing or completing selected tasks or steps manually, automatically, or a combination thereof. Moreover, according to actual instrumentation and equipment of preferred embodiments of the method and apparatus of the present invention, several selected steps could be implemented by hardware or by software on any operating system of any firmware or a combination thereof. For example, as hardware, control of selected steps of the invention could be implemented as a chip or a circuit. As software, control of selected steps of the invention could be implemented as a plurality of software instructions being executed by a computer using any suitable operating system. In any case, selected steps of the method of the invention could be described as being controlled by a data processor, such as a computing platform for executing a plurality of instructions.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention relates to system and method for planning a cryoablation procedure and to system and method for facilitating a cryoablation procedure. More particularly, the present invention relates to the use of integrated images displaying, in a common virtual space, a three-dimensional model of a surgical intervention site based on digitized preparatory images of the site from first imaging modalities, simulation images of cryoprobes used according to an operator-planned cryoablation procedure at the site, and real-time images provided by second imaging modalities during cryoablation. The present invention further relates to system-supplied recommendations for and evaluations of the planned cryoablation procedure, and to system-supplied feedback to an operator and system-supplied guidance and control signals for operating a cryosurgery tool during cryoablation. The present invention still further relates to methods for generating a nearly-uniform cold field among a plurality of cryoprobes, for cryoablating a volume with smooth and well-defined borders.

For purposes of better understanding the present invention, reference is first made to the construction and operation of conventional (i.e., prior art) systems as illustrated in FIGS. 1-10.

Figure 1A:
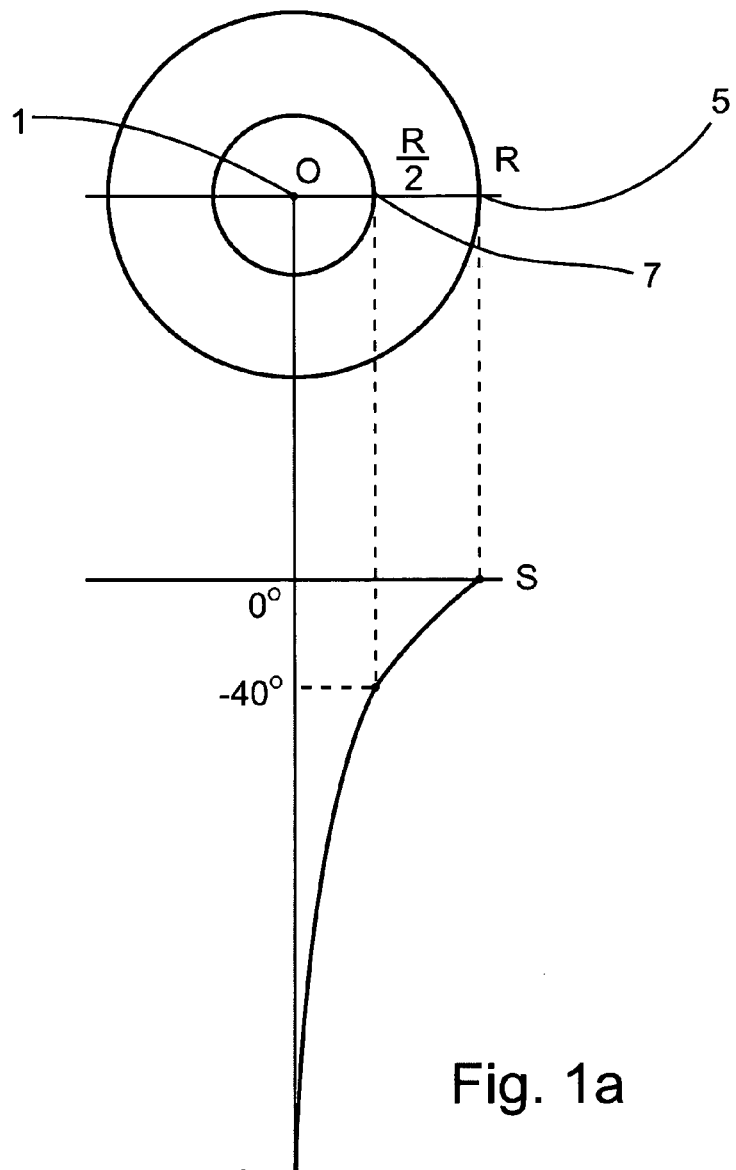
FIG. 1a is a graph showing the profile of temperature distribution within an ice-ball formed at the tip of a cryosurgical probe.

FIG. 1a illustrates the profile of temperature distribution across an ice-ball formed at the tip of a cryosurgical probe. As shown, the temperature at a surface 5 of the ice-ball is 0° C. The temperature declines exponentially towards a center 1 of the ball where it preferably reaches the value of −170° C., such that an isothermal surface 7 of about −40° C. is typically located within the ice-ball at the half way between the center of the ball and its surface. Thus, if the ice-ball features a radius R, then the radius of the −40° C. isothermal surface 7 is about R/2.

Figure 1B:
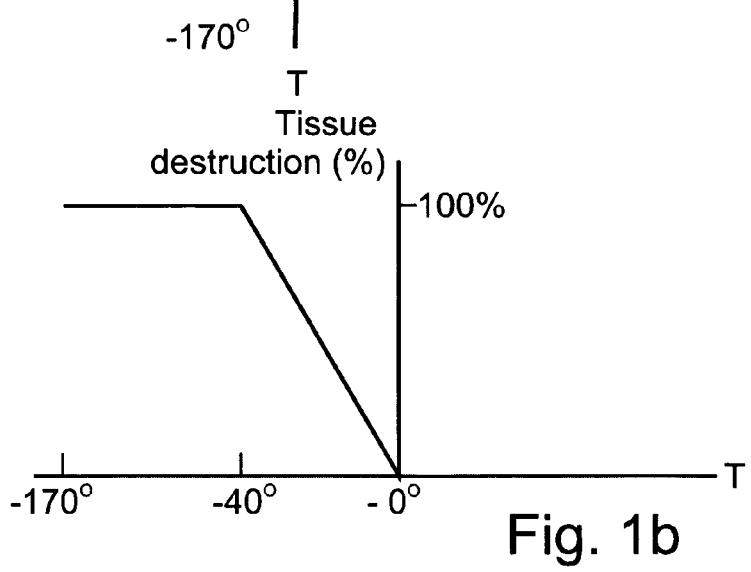
FIG. 1b is a graph showing the effectiveness of a cryosurgical treatment, given in percentage of tissue destruction, as a function of temperature.

FIG. 1b is a graph showing the effectiveness of a cryosurgical treatment (given in percentage of tissue destruction) as a function of temperature. As shown, the temperature required for effectively destroying a tissue is at least about −40° C. Accordingly, in order to effectively destroy a tissue, the isothermal surface of −4° C. (shown in FIG. 1a) should be placed at the periphery of the treated tissue so that the entire area of the treated tissue is exposed to at least about −40° C., thereby exposing adjacent healthy tissues and organs to the external portion of the ice-ball. The application of temperatures of between about −40° C. and 0° C. to such healthy tissues usually causes substantial damage thereto, which damage may result in temporary or permanent impairment of functional organs.

Figure 2A:
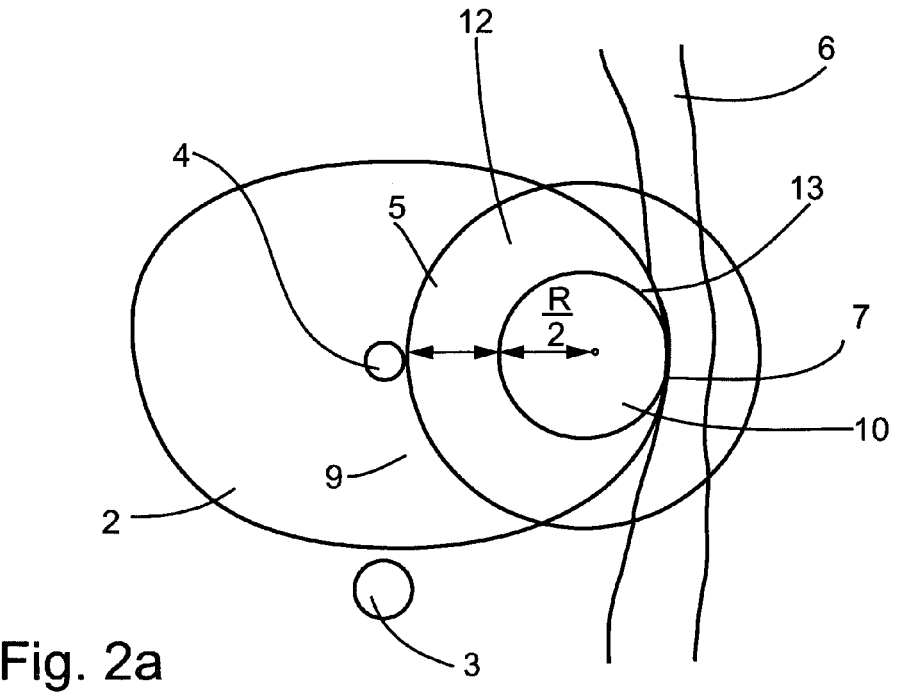
FIGS. 2a-2c are cross sectional views of an ice-ball formed at the tip of a conventional cryosurgical probe introduced into a patient's prostate.
Figure 2B:
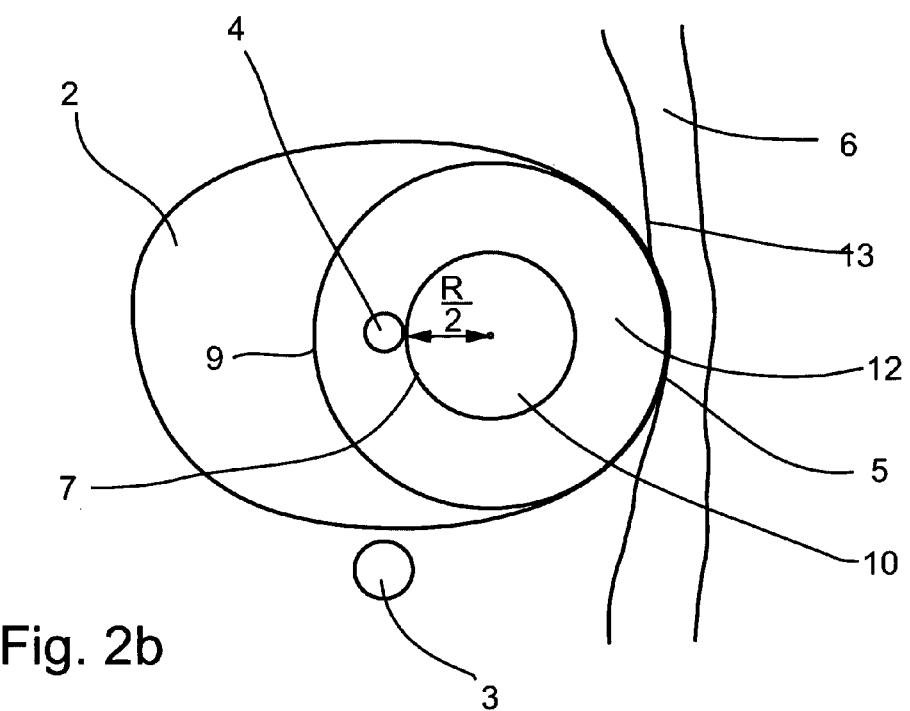
Figure 2C:
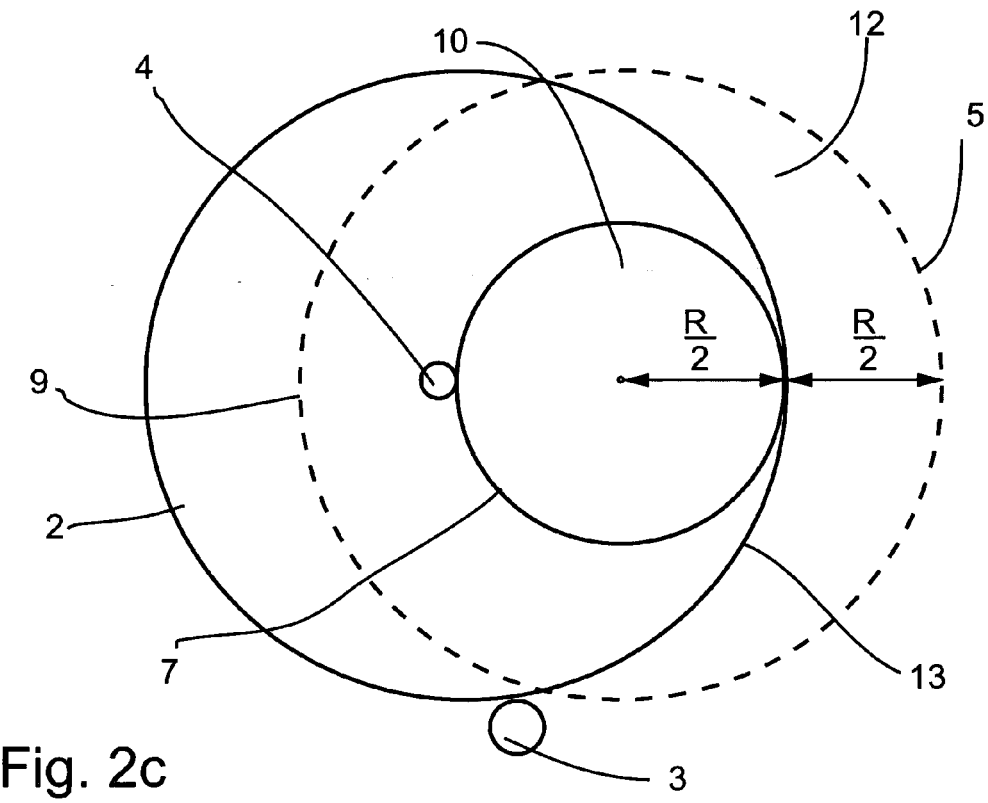

FIGS. 2a-2c illustrate prior-art cryosurgical methods wherein a single cryosurgical probe of a substantially large diameter, typically 3-5 millimeters, is introduced between the patient's prostatic urethra and the periphery of the prostate, so as to destroy the prostatic tissue extending therebetween.

Specifically, FIGS. 2a-2c are cross sectional views of an ice-ball 9 formed at the end of a conventional cryosurgical tip introduced into a prostate 2 of a patient. The patient's prostatic urethra, rectum and nerves are designated as 4, 3, and 6 respectively.

A single ice-ball 9 is formed within the prostatic tissue segment extending between the prostatic urethra 4 and the periphery of the prostate 13. The dimensions of a conventional cryosurgical probe are designed so as to provide an ice-ball 9 having an inner portion 10 extending through a substantially significant portion of such a tissue segment, so as to apply temperatures of between about −170° C. and about −40° C. thereto. The application of a single probe for producing a single ice-ball 9 imposes a trade-off between several options.

FIGS. 2*a* and 2*b* illustrate the trade-off between a first option of avoiding the damaging of the patient's prostatic urethra 4 yet damaging nerves 6 present close to the periphery 13 of the prostate 2 (FIG. 2*a*), and a second option of avoiding the damaging of the patient's nerves 6 yet damaging urethra 4 (FIG. 2*b*).

As shown in FIG. 2*a*, the isothermal surface 7 of −40° C. is positioned substantially at the periphery 13 of the patient's prostate 2, such that surface 5 of the ice-ball 9 is positioned substantially near the patient's urethra 4, so as to avoid damaging of the patient's urethra 4. Thus, the inner portion 10 of ice-ball 9 effectively freezes the peripheral regions (in cross section) of the prostate, while outer portion 12 of ice-ball 9 extends through the patient's nerves 6. The application of temperatures of between about −40° C. and 0° C. to the patient's nerves 6 may result in temporary or permanent impairment thereof.

Similarly, when ice-ball 9 is positioned between the patient's urethra 4 and rectum 3 in such a manner so as to avoid the damaging of urethra 4, the application of between about −40° C. and 0° C. to the patient's rectum may result in temporary or permanent impairment thereof.

As shown in FIG. 2*b*, the isothermal surface 7 of −40° C. is positioned substantially near the patient's urethra 4 such that surface 5 of ice-ball 9 is positioned substantially near the patient's nerves 6 and/or rectum 3 (not shown), so as to avoid damaging of the patient's nerves 6 and/or rectum 3. Thus, inner portion 10 of ice-ball 9 effectively freezes the central regions (in cross section) of prostate 2, while outer portion 12 of ice-ball 9 extends through the patient's urethra 4. The application of temperatures of between about −40° C. and 0° C. to the patient's urethra 4 may result in temporary or permanent impairment thereof.

However, none of the alternatives shown in FIGS. 2*a* and 2*b* provides an effective treatment (temperature of at least about −40° C.) to the entire prostatic tissue segment extending between urethra 4 and the periphery 13 of the prostate, thereby exposing the patient to the risk of malignancy.

FIG. 2*c* shows another possible alternative wherein a thicker cryosurgical probe, having a tip diameter of between 4 and 6 millimeters is used for producing a lager ice-ball, of about 4-5 centimeters in diameter, so as to enable effective treatment of the entire prostatic tissue segment extending between the urethra 4 and periphery 13 of prostate 2. As shown, inner portion 10 of the ice-ball 9 extends through the entire tissue segment (in cross section) between urethra 4 and periphery 13 of the prostate, thereby exposing urethra 4 and nerves (not shown), as well as the rectum 3, to outer portion 12 of the ice-ball 9.

The thickness (in cross section) of tissues exposed to outer portion 12 of the ice-ball is about R/2, wherein R is the radius of ice-ball 9. Thus, the volume of adjacent tissues exposed to damage becomes substantially greater than the volume of the treated tissue.

Thus, the conventional cryosurgical probes and methods fail to provide the necessary resolution of treatment required for enabling an accurate and effective destruction of a tissue while preserving other tissues and organs adjacent thereto.

Figure 3A:
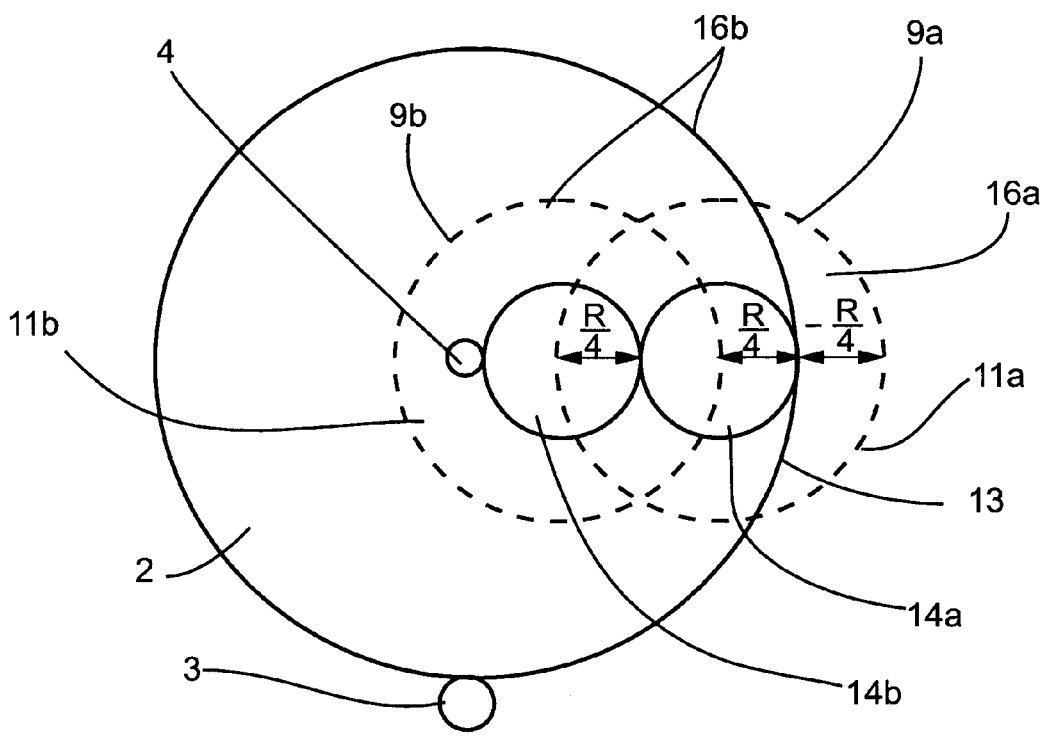
FIGS. 3a-3b are cross sectional views of two ice-balls formed at the tips of cryosurgical probes introduced into a patient's prostate, according to methods of the prior art.
Figure 3B:
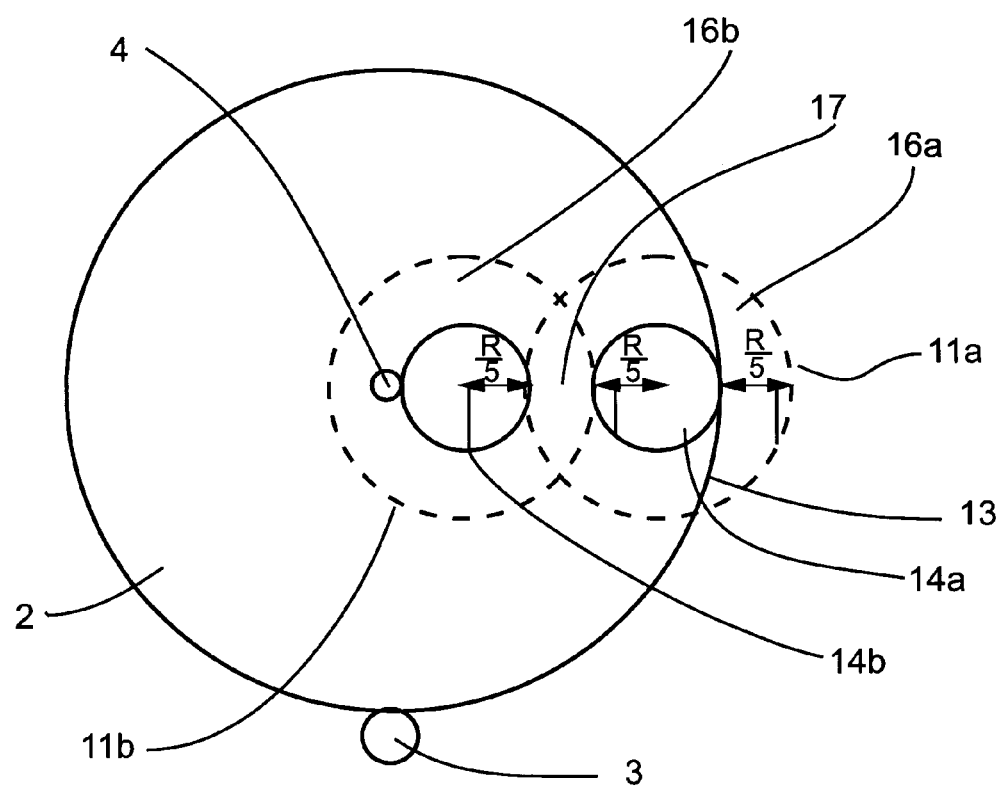

FIGS. 3*a* and 3*b* are schematic illustrations of a cryosurgical method according to another method of prior art, wherein a plurality of cryosurgical probes of substantially small diameters are introduced between the patient's prostatic urethra 4 and periphery 13 of prostate 2, so as to destroy the prostatic tissue extending therebetween.

As shown in FIG. 3*a*, preferably two probes are introduced into a prostatic tissue segment extending between the patient's prostatic urethra 4 and periphery 13 of prostate 2, so as to form two smaller ice-balls, 9*a* and 9*b*.

According to the configuration shown in FIG. 3*a*, each of ice-balls 9*a* and 9*b* features a radius of R/2, which is half the radius of ice-ball 9 shown in FIG. 2*c*. Accordingly, ice-balls 9*a* and 9*b* include respective inner portions, 14*a* and 14*b*, each having a radius of R/4, and respective outer portions, 16*a* and 16*b*, each having a thickness of R/4.

Therefore, by introducing two probes of a small diameters rather than a single probe of a larger diameter into the tissue segment extending between prostatic urethra 4 and periphery 13 of prostate 2, the thickness of adjacent tissues exposed to damage is substantially decreased. The specific example of FIG. 3*a* shows that the thickness (in cross section) of adjacent tissues exposed to between about −40° C. and 0° C. is only R/4, which is half the thickness and respectively much less the volume (e.g., 8 fold less), exposed to damage when using the prior art method (shown in FIG. 2*c*).

By further decreasing the diameter of the cryosurgical probes and introducing a plurality of probes into the tissue segment extending between urethra 4 and periphery 13 of prostate 2, the damage to surrounding tissues may be further minimized, thereby improving the resolution of the cryosurgical treatment.

Another prior art embodiment is shown in FIG. 3*b*, wherein two probes are introduced into the tissue segment extending between the patient's urethra 4 and periphery 13 of prostate 2, so as to form two ice-balls 9*a* and 9*b*, such that inner portion 14*a* of ice-ball 9*a* is substantially spaced from inner portion 14*b* of ice-ball 9*b*, and outer portion 16*a* of ice-ball 9*a* partially overlaps outer portion 16*b* of ice-ball 9*b*, the overlapping region being designated as 17. The specific example shown in FIG. 3*b* is of two ice-balls each having a radius of R/5, wherein R is the radius of a conventional ice-ball as shown in FIG. 2*c*. By using such configuration, the thickness of adjacent tissues exposed to damage is decreased to R/5 and the volume thereof is decreased respectively. It will be appreciated that in the example given substantial fractions of region 17, from which heat is extracted by two probes, will become cooler than −40° C.

The specific examples shown in FIGS. 3*a* and 3*b* are of two ice-balls having tangent and spaced inner portions, respectively. However, a plurality of probes may be used, each having a distinct diameter, the inner portions of which being tangent or spaced.

Figure 4:
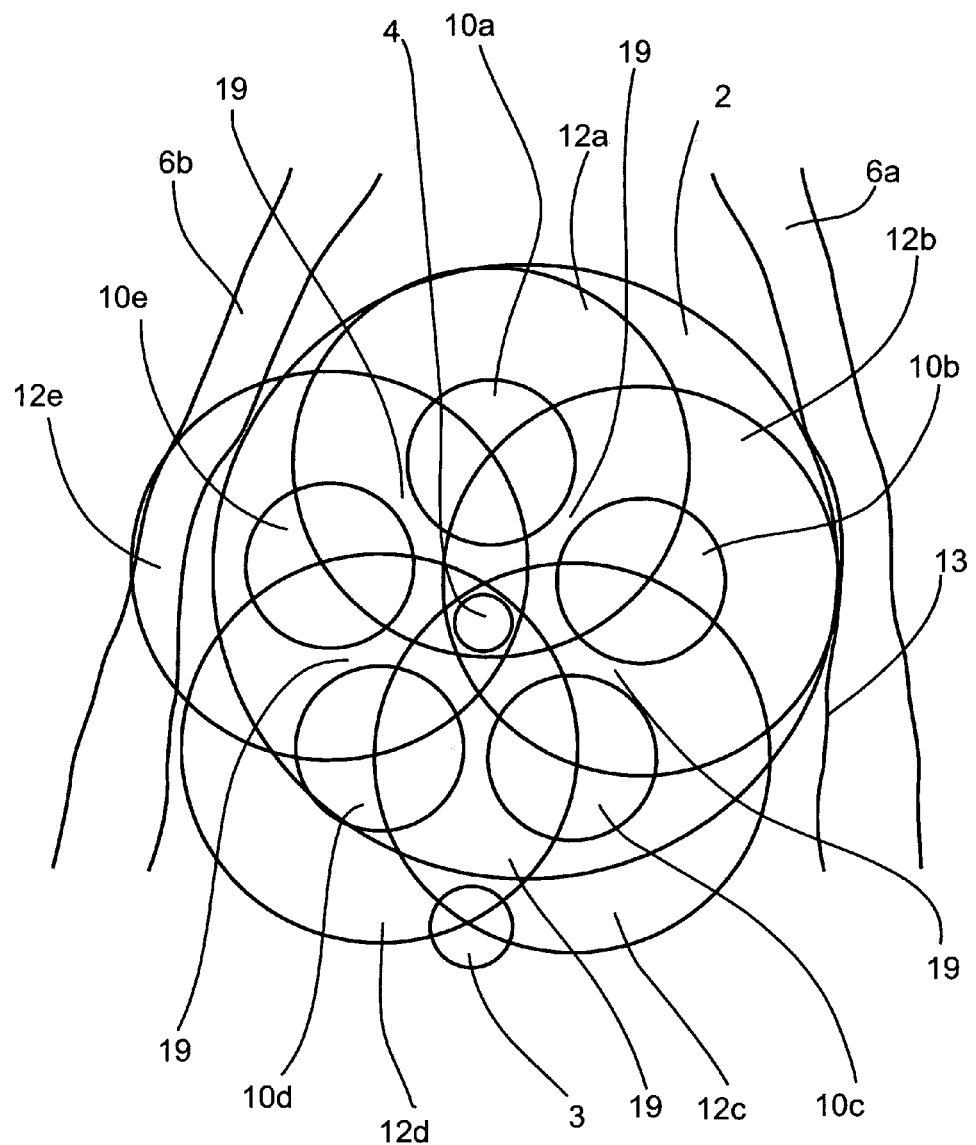
FIG. 4 is a cross sectional view illustrating a method for treating a patient's prostate, according to methods of the prior art.

Referring to FIG. 4, a prior-art cryosurgical method is shown, illustrating the distribution of a plurality of cryosurgical probes across a patient's prostate, wherein a single probe is introduce into a tissue segment extending between prostatic urethra 4 and periphery 13 of prostate 2. According to such a prior art method, about 5-7 probes are introduced into the patient's prostate, wherein each of the probes features a diameter of about 3 millimeters. FIG. 4 shows a specific example wherein five probes are introduced so as to form five ice-balls having inner portions 10*a*-10*e* and outer portions 12*a*-12*e*. As shown, an effective treatment is provided by inner portions 10*a*-10*e*, and regions therebetween marked 19, only to limited regions of the prostate, wherein the damage caused to adjacent tissues such as the patient's urethra 4, rectum 3 and nerve 6*b* by outer portions 12*a*-12*e* is considerable.

Figure 5:
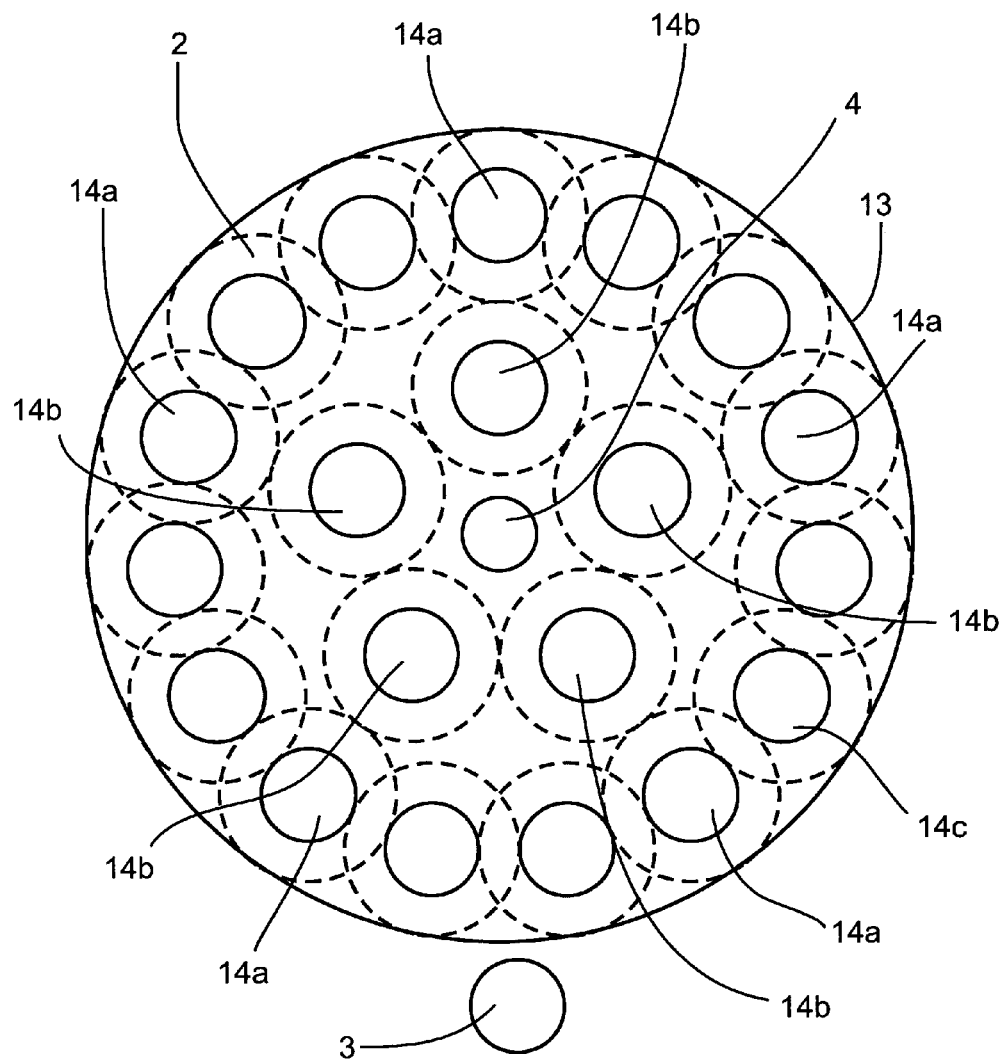
FIG. 5 is a cross sectional view illustrating a further method for treating a patient's prostate, according to methods of the prior art.
Figure 6:
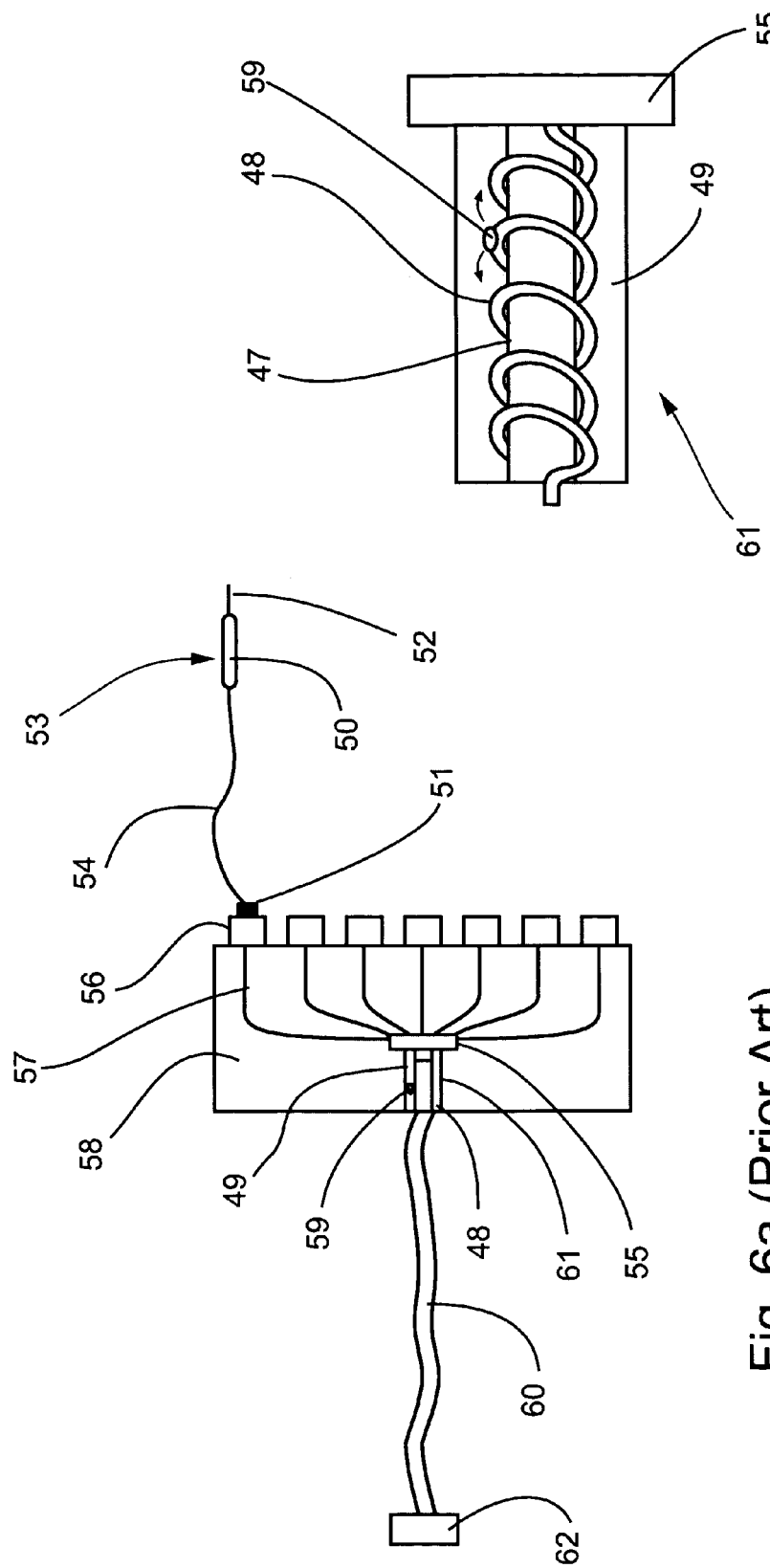
FIG. 6a is a schematic illustration of a multi-probe cryosurgical device according to methods of the prior art.
FIG. 6b is a schematic illustration of a pre-cooling element according to methods of the prior art.

FIG. 5 shows a preferred distribution of cryosurgical probes according to another method of prior art. As shown, at least two cryosurgical probes of substantially small diameter are introduced into specific segments of prostatic tissue extending between urethra 4 and periphery 13 of prostate 2. FIG. 5 shows a specific example wherein twenty probes are introduced into the patient's prostate 2, including five pairs of inner and outer cryosurgical probes located at specific segments of the prostate extending from the urethra 4 to periphery 13, and additional (five pairs in the example given) of outer cryosurgical probes are introduced therebetween. The inner portions of the ice-balls formed by the pairs of outer and inner probes are designated as 14a and 14b, respectively, wherein the inner portions of the ice-balls formed therebetween are designated as 14c.

The diameter of a single cryosurgical probe according to the prior art method presented in FIG. 5 is preferably between about 1.2 millimeters and about 1.4 millimeters.

As shown, such distribution of substantially small diameter cryosurgical probes enables to provide an effective treatment of at least −40° C. to a larger area of the prostatic tissue while substantially minimizing the thickness of healthy adjacent tissues exposed to damage.

Thus, the prior art method presented in FIG. 5 substantially increases the effectiveness and resolution of treatment relative to the prior art method presented by FIG. 4.

The pattern of distribution of probes shown in FIG. 5 includes an inner circle and an outer circle of probes, wherein a portion of the probes is arranged in pairs of an inner probe and an outer probe. According to another configuration (not shown), the probes are arranged in an inner circle and an outer circle, but not necessarily in pairs of an inner probe and an outer probe.

The probes may be sequentially introduced to and extracted from the patient's prostate so as to sequentially freeze selected portions thereof. A method of quick extraction of the probes without tearing pieces of tissue from the patient, which stick to the tip of the probe, is disclosed hereinunder.

The introduction of a plurality of small diameter cryosurgical probes improves the resolution of treatment along the planes perpendicular to the axis of penetration of the probes into the prostate. However, the prostate, as other anatomical organs, features an asymmetric three dimensional shape. Thus, a specific pattern of distribution of probes may provide an effective treatment to a distinct plane located at a specific depth of penetration, but at the same time may severely damage non-prostatic tissues located at other depths of penetration. There is need for cryosurgical method and apparatus which enable high resolution of treatment along and perpendicular to the axis of penetration of the probes into a patient's organ. Presented hereinbelow is a cryosurgical method and apparatus according to prior art which enable high resolution of treatment along the axis of penetration of the cryosurgical probe into the patient's organ as well as along the planes perpendicular to the axis of penetration, wherein these high resolutions are achieved by forming a three-dimensional grid of the organ, preferably by using ultrasound imaging, and inserting each of the cryosurgical probes to a specific depth within the organ according to the information provided by the grid.

Figure 7:
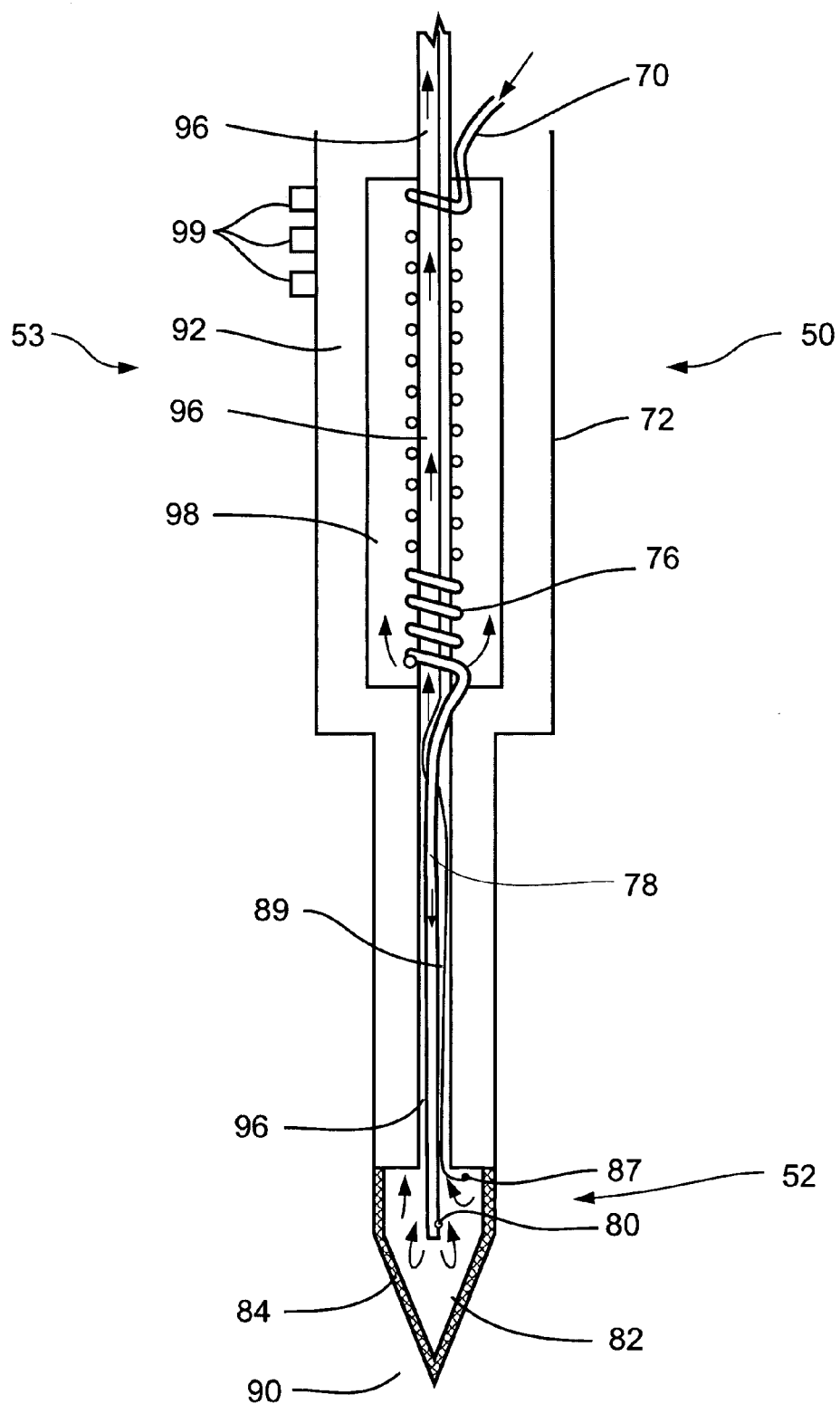
FIG. 7 is a schematic longitudinal section of a preferred cryosurgical probe according to methods of the prior art.

Referring to FIGS. 6a, 6b and 7, a cryosurgical apparatus according to methods of prior art includes a plurality of cryosurgical probes 53, each having an operating tip 52 including a Joule-Thomson cooler for freezing a patient's tissue and a holding member 50 for holding by a surgeon. As shown in FIG. 7, operating tip 52 includes at least one passageway 78 extending therethrough for providing gas of high pressure to orifice 80 located at the end of operating tip 52, orifice 80 being for passage of high pressure gas therethrough, so as to cool operating tip 52 and produce an ice-ball at its end 90.

Gases which may be used for cooling include, but are not limited to argon, nitrogen, air, krypton, $CO_2$, $CF_4$, xenon, or $N_2O$.

When a high pressure gas such as argon expands through orifice 80 it liquefies, so as to form a cryogenic pool within chamber 82 of operating tip 52, which cryogenic pool effectively cools surface 84 of operating tip 52. Surface 84 of operating tip 52 is preferably made of a heat conducting material such as metal so as to enable the formation of an ice-ball at end 90 thereof.

Alternatively, a high pressure gas such as helium may be used for heating operating tip 52 via a reverse Joule-Thomson process, so as to enable treatment by cycles of cooling-heating, and further for preventing sticking of the probe to the tissue when extracted from the patient's body, and to enable fast extraction when so desired.

When a high pressure gas such as helium expands through orifice 80 it heats chamber 82, thereby heating surface 84 of operating tip 52.

Operating tip 52 includes at least one evacuating passageway 96 extending therethrough for evacuating gas from operating tip 52 to the atmosphere.

As shown FIG. 7, holding member 72 may include a heat exchanger for pre-cooling the gas flowing through passageway 78. Specifically, the upper portion of passageway 78 may be in the form of a spiral tube 76 wrapped around evacuating passageway 96, the spiral tube being accommodated within a chamber 98. Thus, gas evacuated through passageway 96 may pre-cool the incoming gas flowing through spiral tube 76.

As further shown in FIG. 7, holding member 72 may include an insulating body 92 for thermally insulating the heat exchanger from the external environment.

Furthermore, operating tip 52 may include at least one thermal sensor 87 for sensing the temperature within chamber 82, the wire 89 of which extending through evacuating passageway 96 or a dedicated passageway (not shown).

In addition, holding member 72 may include a plurality of switches 99 for manually controlling the operation of probe 53 by a surgeon. Such switches may provide functions such as on/off, heating, cooling, and predetermined cycles of heating and cooling by selectively and controllably communicating incoming passageway 70 with an appropriate external gas container including a cooling or a heating gas.

As shown in FIG. 6a, each of cryosurgical probes 53 is connected via a flexible connecting line 54 to a connecting site 56 on a housing element 58, preferably by means of a linking element 51. Cryosurgical probes 53 may be detachably connected to connecting sites 56.

Preferably, evacuating passageway 96 extends through connecting line 54, such that the outgoing gas is evacuated through an opening located at linking element 51 or at any other suitable location, e.g., manifold 55, see below. Preferably, line 54 further includes electrical wires for providing electrical signals to the thermal sensor and switches (not shown).

Each of cryosurgical probes 53 is in fluid communication with a manifold 55 received within a housing 58, manifold 55 being for distributing the incoming high pressure gas via lines 57 to cryosurgical probes 53.

As shown, housing 58 is connected to a connector 62 via a flexible cable 60 including a gas tube (not shown), connector 62 being for connecting the apparatus to a high pressure gas source and an electrical source.

The apparatus further includes electrical wires (not shown) extending through cable 60 and housing 58 for providing electrical communication between the electrical source and cryosurgical probes 53.

Preferably, housing 58 includes a pre-cooling element, generally designated as 61, for pre-cooling the high pressure gas flowing to cryosurgical probes 53. Preferably, pre-cooling element 61 is a Joule-Thomson cooler, including a tubular member 48 received within a chamber 49, tubular member 48 including an orifice 59 for passage of high pressure gas therethrough, so as to cool chamber 49, thereby cooling the gas flowing through tubular member 48 into manifold 55.

Another configuration of a pre-cooling element 61 is shown in FIG. 6b, wherein tubular member 48 is in the form of a spiral tube wrapped around a cylindrical element 47, so as to increase the area of contact between tubular member 48 and the cooling gas in chamber 49.

According to yet another configuration (not shown), housing 58 includes a first tubular member for supplying a first high pressure gas to manifold 55, and a second tubular member for supplying a second high pressure gas to pre-cooling element 61. Any combination of gases may be used for cooling and/or heating the gases flowing through such tubular members.

Alternatively, a cryogenic fluid such as liquid nitrogen may be used for pre-cooling the gas flowing through housing 58. Alternatively, an electrical pre-cooling element may used for pre-cooling the gas.

Preferably, thermal sensors (not shown) may be located within cable 60 and manifold 55 for measuring the temperature of gas flowing therethrough.

Figure 8:
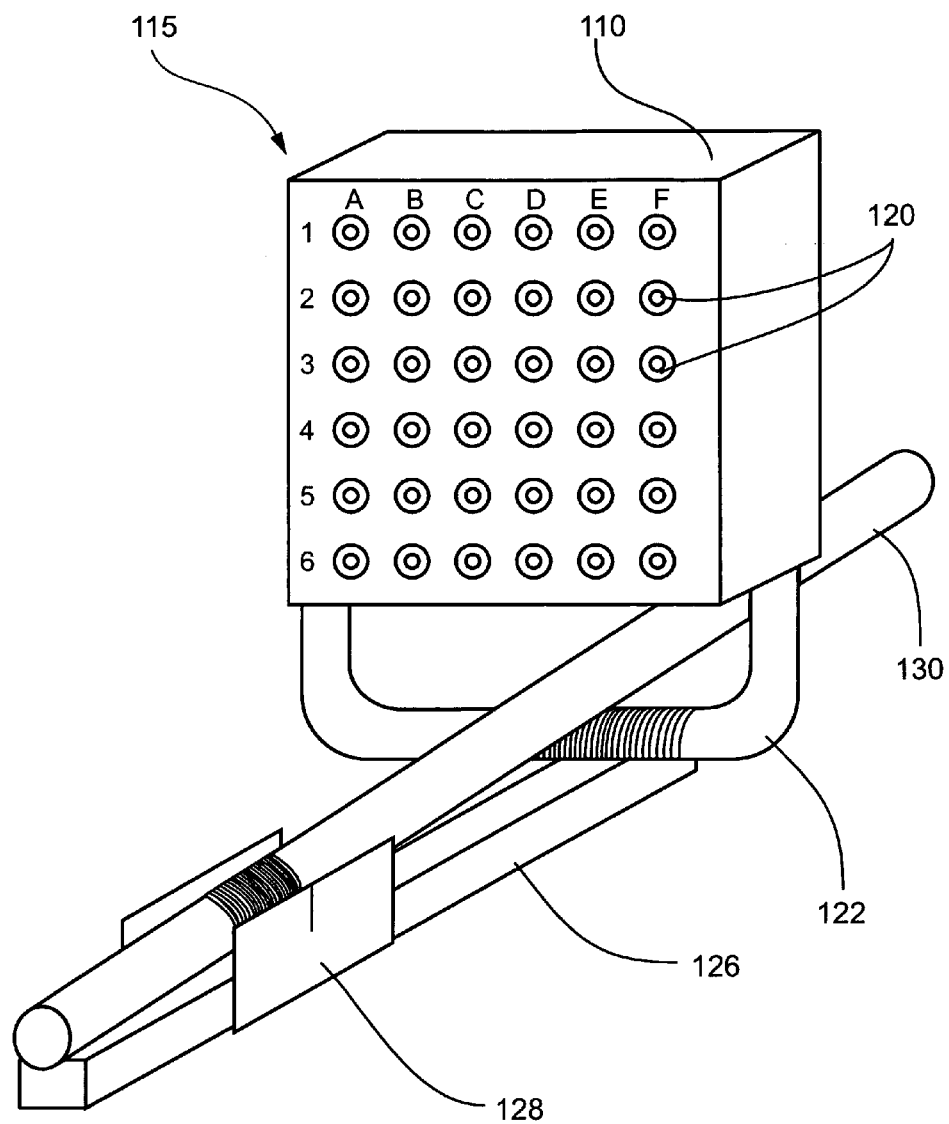
FIG. 8 is a perspective view of a guiding element for receiving cryosurgical probes, the guiding element being connected to an ultrasound probe, according to methods of the prior art.
Figure 9:
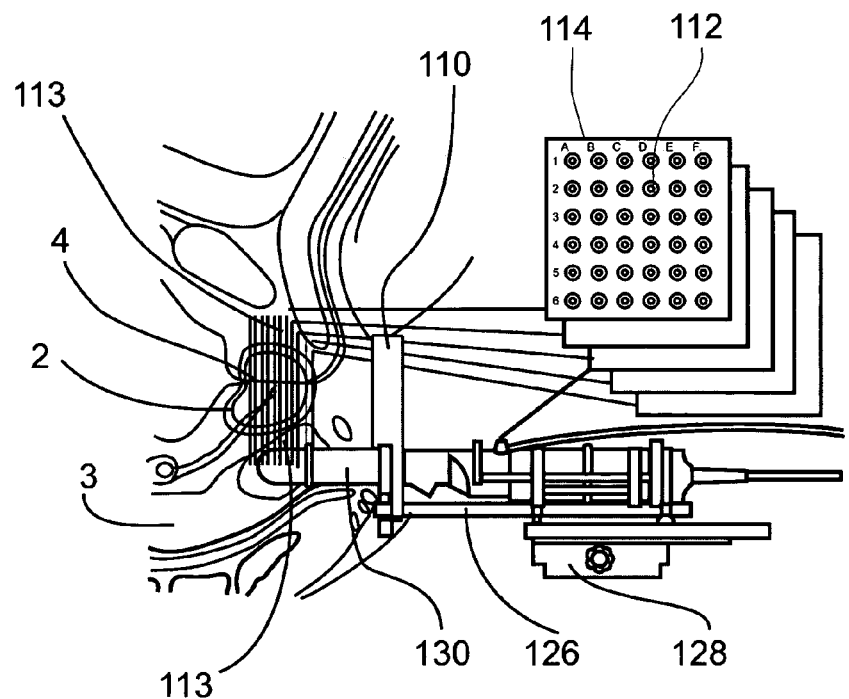
FIGS. 9 and 10 illustrate a method including the steps of forming a three-dimensional grid of a patient's prostate and introducing cryosurgical probes thereto, according to methods of the prior art.
Figure 10:
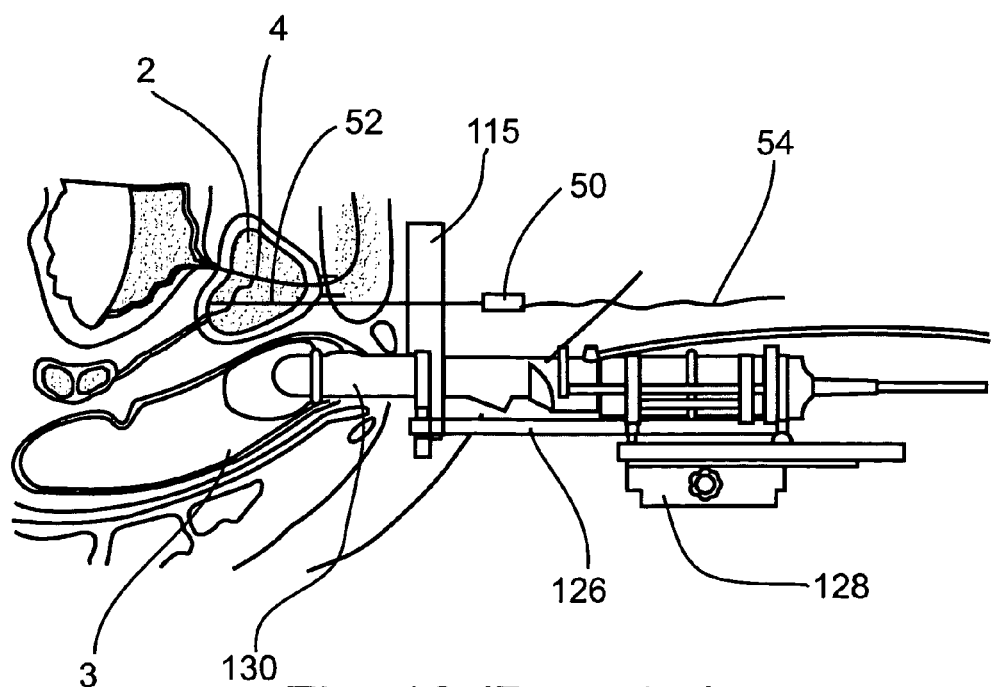

Referring to FIGS. 8-10, method and apparatus according to prior art applies an imaging device such as ultrasound, MRI or CT, so as to form a three-dimensional grid of the patient's treated organ, e.g., prostate, the three dimensional grid serves for providing information on the three dimensional shape of the organ. Each of the cryosurgical probes is then inserted to a specific depth within the organ according to the information provided by the grid.

As shown in FIG. 8, an ultrasound probe 130 is provided for insertion into the patient's rectum, ultrasound probe 130 being received within a housing element 128. A guiding element 115 is connected to housing element 128 by means of a connecting arm 126. As shown, guiding element 115 is in the form of a plate 110 having a net of apertures 120, each aperture serves for insertion of a cryosurgical probe therethrough. Preferably, the distance between each pair of adjacent apertures 120 is between about 2 millimeters and about 5 millimeters.

As shown in FIG. 9, ultrasound probe 130 is introduced to a specific depth 113 within the patient's rectum 3. A net of marks 112 is provided on the obtained ultrasound image 114, the net of marks 112 on image 114 being accurately correlated to the net of apertures 120 on guiding element 115.

Thus, marks 112 on image 114 sign the exact locations of the centers of ice-balls which may be formed at the end of the cryosurgical probes inserted through apertures 120 to the patient's prostate 2, wherein image 114 relates to a specific depth of penetration 113 of the cryosurgical probes into the prostate 2.

As shown in FIG. 9, ultrasound probe 130 is gradually introduced to various depths 113 of rectum 3, thereby producing a set of images 114, wherein each image relates to a respective depth of penetration into the prostate 2. Thus, each of images 114 relates to a specific plane perpendicular to the axis of penetration of the cryosurgical probes.

The set of images 114 provides a three dimensional grid of the prostate. Such three-dimensional grid is then used for planning the cryosurgical procedure.

For example, the introduction of a cryosurgical probe along a given axis of penetration to a first depth may effectively destroy a prostatic tissue segment, while introduction of the probe to a second depth may severely damage the prostatic urethra.

Since the ice-ball is locally formed at the end of the cryosurgical probe, each probe may be introduced to a specific depth so as to locally provide an effective treatment to a limited portion of the prostate while avoiding the damaging of non-prostatic or prostatic tissues located at other depths of penetration.

FIG. 10 shows the insertion of an operating tip 52 of a cryosurgical probe 50 through an aperture of guiding element 115 into the prostate 2 of a patient.

Preferably, a plurality of cryosurgical probes are sequentially inserted through apertures 120 of guiding element 115 into the patient's prostate, wherein each probe is introduced to a specific depth, thereby providing substantially local effective treatment to distinct segments of the prostatic tissue while avoiding the damaging of other prostatic or nonprostatic tissue segments.

Preferably, each of the cryosurgical probes includes a scale for indicating the depth of penetration into the prostate.

Figure 11:
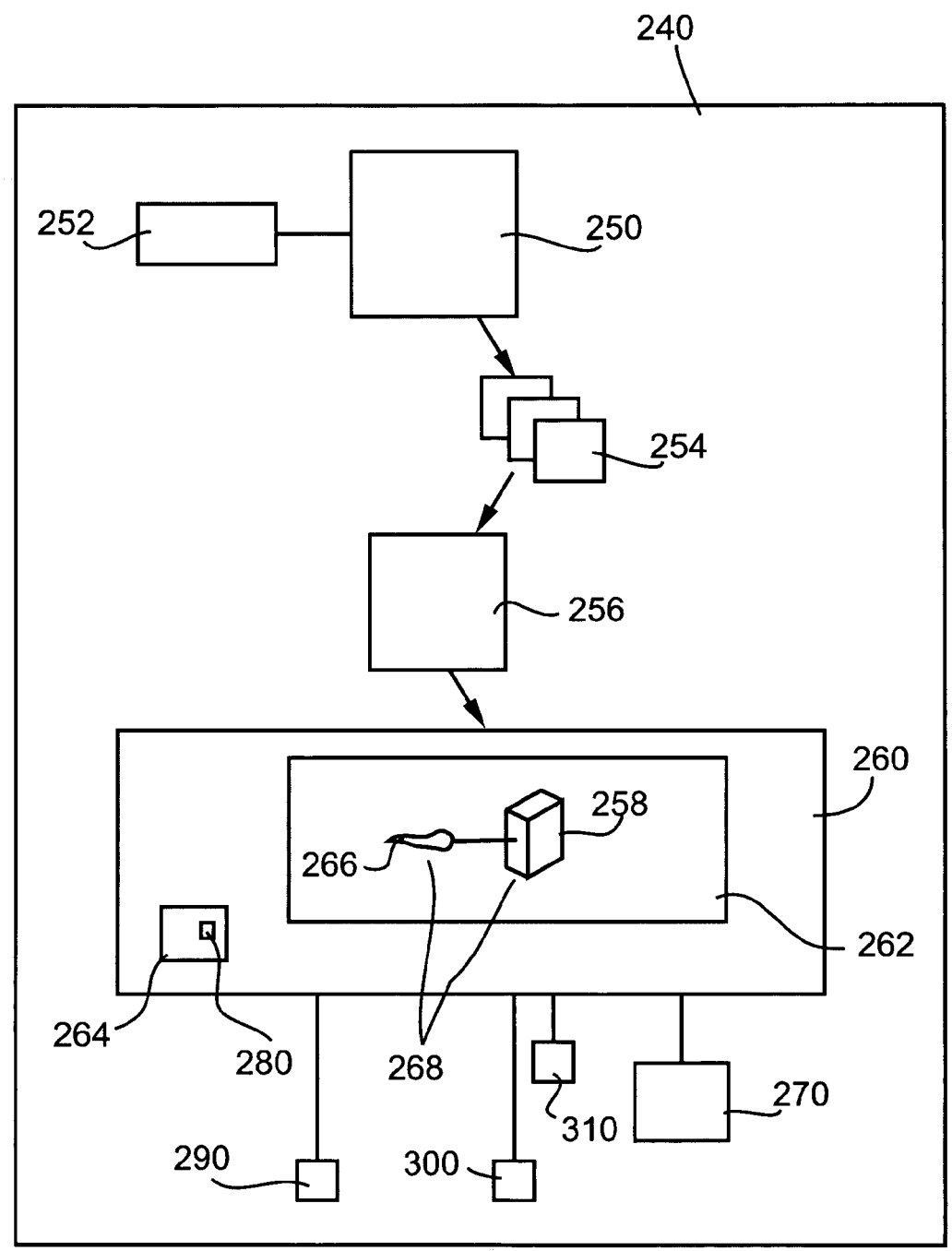
FIG. 11 is a simplified block diagram of a planning system for planning a cryoablation procedure, according to a first preferred embodiment of the present invention.

Reference is now made to FIG. 11, which is a simplified block diagram of a planning system for planning a cryoablation procedure, according to a first preferred embodiment of the present invention.

In FIG. 11, a planning system 240 for planning a cryoablation procedure comprises a first imaging modality 250 which serves for creating digitized preparatory images 254 of a cryoablation intervention site. First imaging modality 250 will typically be a magnetic resonance imaging system (MRI), an ultrasound imaging system, a computerized tomography imaging system (CT), a combination of these systems, or a similar system able to produce images of the internal tissues and structures of the body of a patient. First imaging modality 250 is for producing digitized images of a cryoablation intervention site, which site includes body tissues whose cryoablation is desired (referred to herein as "target" tissue), which may be a tumor or other structure, and body tissues and structures in the immediate neighborhood of the target tissues, which constitute the target tissue's physical environment.

Some types of equipment useable as first imaging modality 250, a CT system for example, typically produce a digitized image in a computer-readable format. If equipment used as first imaging modality 250 does not intrinsically produce digitized output, as might be the case for conventional x-ray imaging, then an optional digitizer 252 may be used to digitize non-digital images, to produce digitized preparatory images 254 of the site.

Digitized images 254 produced by first imaging modality 250 and optional digitizer 252 are passed to a three-dimensional modeler 256 for creating a three-dimensional model 258 of the intervention site. Techniques for creating a three dimensional model based on a set of two dimensional images are well known in the art. In the case of CT imaging, creation of a three dimensional model is typically an intrinsic part of the imaging process. PROVISION, from Algotec Inc. (http://www.algotec.com/products/provision.htm) is an example of software designed to make a 2-D to 3-D conversion for images generated by CT scans. To accomplish the same purpose starting from ultrasound imaging, SONOReal™ software from BIOMEDICOM (http://www.biomedicom.com/) may be used.

Three dimensional model 258 is preferably expressible in a three dimensional Cartesian coordinate system.

Three dimensional model 258 is useable by a simulator 260 for simulating a cryosurgical intervention. Simulator 260 comprises a displayer 262 for displaying views of model 258, and an interface 264 useable by an operator for specifying loci for insertion of simulated cryoprobes 266 and operational parameters for operation of simulated cryoprobes 266 for cryoablating tissues. Thus, an operator (i.e., a user) can use simulator 260 to simulate a cryoablation intervention, by using interface 264 to command particular views of model 258, and by specifying both where to insert simulated cryoprobes 266 into an organ imaged by model 258, and how to operate cryoprobes 266. Typically, an operator may specify positions for a plurality of simulated cryoprobes 266, and further specify operating temperatures and durations of cooling for cryoprobes 266. Display 262 is then useable for displaying in a common virtual space an integrated image 268 comprising a display of three dimensional model 258 and a virtual display of simulated cryoprobes 266 inserted at said operator-specified loci.

Planning system 240 optionally comprises a memory 270, such as a computer disk, for storing operator-specified loci for insertion of cryoprobes and operator-specified parameters for operation simulated cryoprobes 266.

Interface 264 comprises a highlighter 280 for highlighting, under control of an operator, selected regions within three dimensional model 258. Operator-highlighted selected regions of model 258 are then optionally displayed as part of an integrated image 268.

In particular, highlighter 280 is useable by an operator for identifying tissues to be cryoablated. Preferably, interface 264 permits an operator to highlight selected regions of three dimensional model 258 so as to specify therein tissues to be cryoablated, or alternatively interface 264 permits an operator to highlight selected regions of digitized preparatory images 254, specifying therein tissues to be cryoablated. In the latter case, three-dimensional modeler 256 is then useable to translate regions highlighted on digitized preparatory images 254 into equivalent regions of three dimensional model 258. In both cases, tissues highlighted and selected to be cryoablated can be displayed by displayer 262 as part of integrated image 268, and can be recorded by memory 270 for future display or other uses.

Similarly, highlighter 280 is useable by an operator for identifying tissues to be protected from damage during cryoablation. Typically, important functional organs not themselves involved in pathology may be in close proximity to tumors or other structures whose destruction is desired. For example, in the case of cryoablation in a prostate, nerve bundles, the urethra, and the rectum may be in close proximity to tissues whose cryoablation is desired. Thus, highlighter 280 is useable by an operator to identify (i.e., to specify the location of) such tissues and to mark them as requiring protection from damage during cryoablation.

Preferably, interface 264 permits an operator to highlight selected regions of three dimensional model 258 so as to specify therein tissues to be protected from damage during cryoablation. Alternatively, interface 264 permits an operator to highlight selected regions of digitized preparatory images 254, specifying therein tissues to be protected during cryoablation. In the latter case, three-dimensional modeler 256 is then useable to translate regions highlighted on digitized preparatory images 254 into equivalent regions of three dimensional model 258. In both cases, tissues highlighted and selected to be protected from damage during cryoablation can be displayed by displayer 262 as part of integrated image 268, and can be recorded by memory 270 for future display or other uses.

Planning system 240 further optionally comprises a predictor 290, an evaluator 300, and a recommender 310.

Predictor 290 serves for predicting the effect on tissues of a patient, if a planned operation of cryoprobes 266 at the operator-specified loci is actually carried out according to the operator-specified operational parameters. Predictions generated by predictor 290 may optionally be displayed by displayer 262 as part of integrated image 268, in the common virtual space of image 268.

In a preferred embodiment, predictions of predictor 290 are based on several sources. The laws of physics, as pertaining to transfer of heat, provide one predictive source. Methods of calculation well known in the art may be used to calculate, with respect to any selected region within three dimensional model 258, a predicted temperature, given known locations of cryoprobes 266 which are sources of cooling in proximity to such a region, known temperatures and cooling capacities of cryoprobes 266, and a duration of time during which cryoprobes 266 are active in cooling. Thus, a mathematical model based on known physical laws allows to calculate a predicted temperature for any selected region within model 258 under operator-specified conditions.

Experimentation and empirical observation in some cases indicate a need for modifications of a simple mathematical model based on physical laws concerning the transfer of heat, as would be the case, for example, in a tissue wherein cooling processes were modified by a high rate of blood flow. However, methods for adapting such a model to such conditions are also well known in the art. Such methods take into account heat dissipation in flowing systems, effected by the flow.

An additional basis for predictions of predictor 290 is that of clinical observation over time. Table 1 provides an example of a predictive basis derived from clinical observation, relating to medium-term and long-term effects of cryoablation procedures in a prostate. The example provided in Table 1 relates to treatment of BPH by cryoablation under a standardized set of cryoprobe operating parameters.

TABLE 1

| Predicted long-term effects of cryoablation | | |
|---|---|---|
| Distance between probes (mm) | 3 week volume consumption (%) | 3 months volume consumption (%) |
| 10 | 70 | 100 |
| 15 | 55 | 85 |
| 20 | 40 | 70 |
| 25 | 30 | 50 |

As may be seen from Table 1, clinical observation leads to the conclusion that reduction in the volume of a prostate following cryoablation is a gradual process which continues progressively for a number of weeks following a cryoablation procedure. The clinically derived information of Table 1, and similar clinically derived information, can also serve as a basis for predictions generated by predictor 290, and displayed by displayer 262 as part of integrated image 268 in the common virtual space of image 268.

Evaluator 300 is useable to compare results predicted by predictor 290 to goals of a surgical intervention as expressed by an operator. In particular, evaluator 300 can be used to compare intervention results predicted by predictor 290 under a given intervention plan specified by an operator, with that operator's specification of tissues to be cryoablated. Thus, an operator may use interface 264 to specify tissues to be cryoablated, plan an intervention by using interface 264 to specify loci for insertion of cryoprobes 266 and to specify a mode of operation of cryoprobes 266, and then utilize predictor 290 and evaluator 300 to predict whether, under his specified intervention plan, his/her goal will be realized and all tissues desired to be cryoablated will in fact be destroyed. Similarly, an operator may utilize predictor 290 and evaluator 300 to predict whether, under his/her specified intervention plan, tissues which he specified as requiring protection from damage during cryoablation will in fact be endangered by his planned intervention.

Recommender 310 may use predictive capabilities of predictor 290 and evaluator 300, or empirically based summaries of experimental and clinical data, or both, to produce recommendations for cryoablation treatment.

As discussed above, predictor 290 and evaluator 300 can be used to determine, for a given placement of a given number of cryoprobes and for a given set of operating parameters, whether a planned cryoablation procedure can be expected to be successful, success being defined as destruction of tissues specified as needing to be destroyed, with no damage or minimal damage to tissues specified as needing to be protected during cryoablation. Based on this capability, recommender 310 can utilize a variety of calculation techniques well known in the art to evaluate a plurality of competing cryoablation intervention strategies and to express a preference for that strategy which is most successful according to these criteria.

In particular, recommender 310 may consider several intervention strategies proposed by an operator, and recommend the most successful among them. Alternatively, an operator might specify a partial set of operating parameters, and recommender 310 might then vary (progressively or randomly) additional operating parameters to find a 'best fit' solution. For example, an operator might specify tissues to be destroyed, tissues to be protected, and a two-dimensional array of cryoprobes such as, for example, the two dimensional placement array of cryoprobes determined by the use of guiding element 115 having a net of apertures 120 shown in FIG. 8 hereinabove. Recommender 310 could then test a multitude of options for displacements of a set of cryoprobes in a third (depth) dimension to determine the shallowest and deepest penetration desirable for each cryoprobe. Recommender 310 could further be used to calculate a temperature and duration of freezing appropriate for each cryoprobe individually, or for all deployed cryoprobes controlled in unison, in a manner designed to destroy all tissues specified to be destroyed, while maximizing protection of tissues specified to be protected.

Recommendation activity of recommender 310 may also be based on empirical data such as experimental results or clinical results. Table 2 provides an example of a basis for making recommendations derived from clinical observation.

TABLE 2

Recommended number of cryoprobes to treat BPH

| American Urologists Association Questionnaire Score | Number of cross-sections with stricture of the Urethra | Prostate Volume | Number of probes |
|---|---|---|---|
| 0-7 | 1-3 | 25 | 2 |
| 0-7 | 1-3 | 40 | 2 |
| 0-7 | 2-5 | 40 | 2 |
| 0-7 | 1-3 | 50 | 2-3 |
| 0-7 | 2-5 | 50 | 2-3 |
| 0-7 | 1-3 | 60 | 2-3 |
| 0-7 | 2-5 | 60 | 3 |
| 0-7 | 2-5 | 100 | 4 |
| 8-19 | 1-3 | 40 | 2-3 |
| 8-19 | 2-5 | 40 | 2-3 |
| 8-19 | 1-3 | 50 | 2 |
| 8-19 | 2-5 | 50 | 2-3 |
| 8-19 | 1-3 | 60 | 3 |
| 8-19 | 2-5 | 60 | 3-4 |
| 8-19 | 2-5 | 100 | 4 |
| 20-35 | 1-3 | 40 | 3 |
| 20-35 | 2-5 | 40 | 3 |
| 20-35 | 1-3 | 50 | 4 |
| 20-35 | 2-5 | 50 | |
| 20-35 | 1-3 | 60 | 4 |
| 20-35 | 2-5 | 60 | 5 |
| 20-35 | 2-5 | 100 | 6 |

Table 2 relates to the treatment of BPH by cryoablation. Table 2 is essentially a table of expert opinion, wherein three criterions for describing the symptomatic state of a patient are related, by experts, to a recommendation for treatment. Table 2 was in fact compiled by a group of experts in the practice of cryoablation utilizing a particular tool, specifically a tool similar to that described in FIG. 8 hereinabove, yet a similar table may be constructed by other experts and for other tools. Moreover, feedback from the collective clinical experience of a population of users of a particular tool may be collected over time, for example by a company marketing such a tool or by an independent research establishment, and such collected information may be fed back into recommender 310 to build a progressively better informed and increasingly useful and reliable recommendation system.

The first column of Table 2, the AUA score, is the score of a questionaire in use by the American Urological Association which may be found in Tanagho E. A., and McAninich J. W., *Smith's General Urology*, published by McGraw-Hill, Chapter 23. The AUA score is an estimate of severity of symptoms as subjectively reported by a patient, and relates to such urinary problems as incomplete emptying of the bladder, frequency of urination, intermittency, urgency, weak stream, straining, nocturia, and the patient's perceived quality of life as it relates to his urinary problems.

The second and third columns of Table 2 relate to diagnostic criteria discemable from three-dimensional model 258 or from digitized preparatory images 254 from which model 258 derives. The second column is a measure of the length of that portion of the urethra observed to be constricted by pressure from a patient's prostate. The third column is a measure of the volume of that patient's prostate. Table 2 constitutes a basis for recommending an aspect of a cryoablation treatment for BPH, specifically for recommending, in column four, an appropriate number of cryoprobes to be used in treating a specific patient, based on three quantitative evaluations of his condition constituted by the columns one, two and three of Table 2.

Figure 12A:
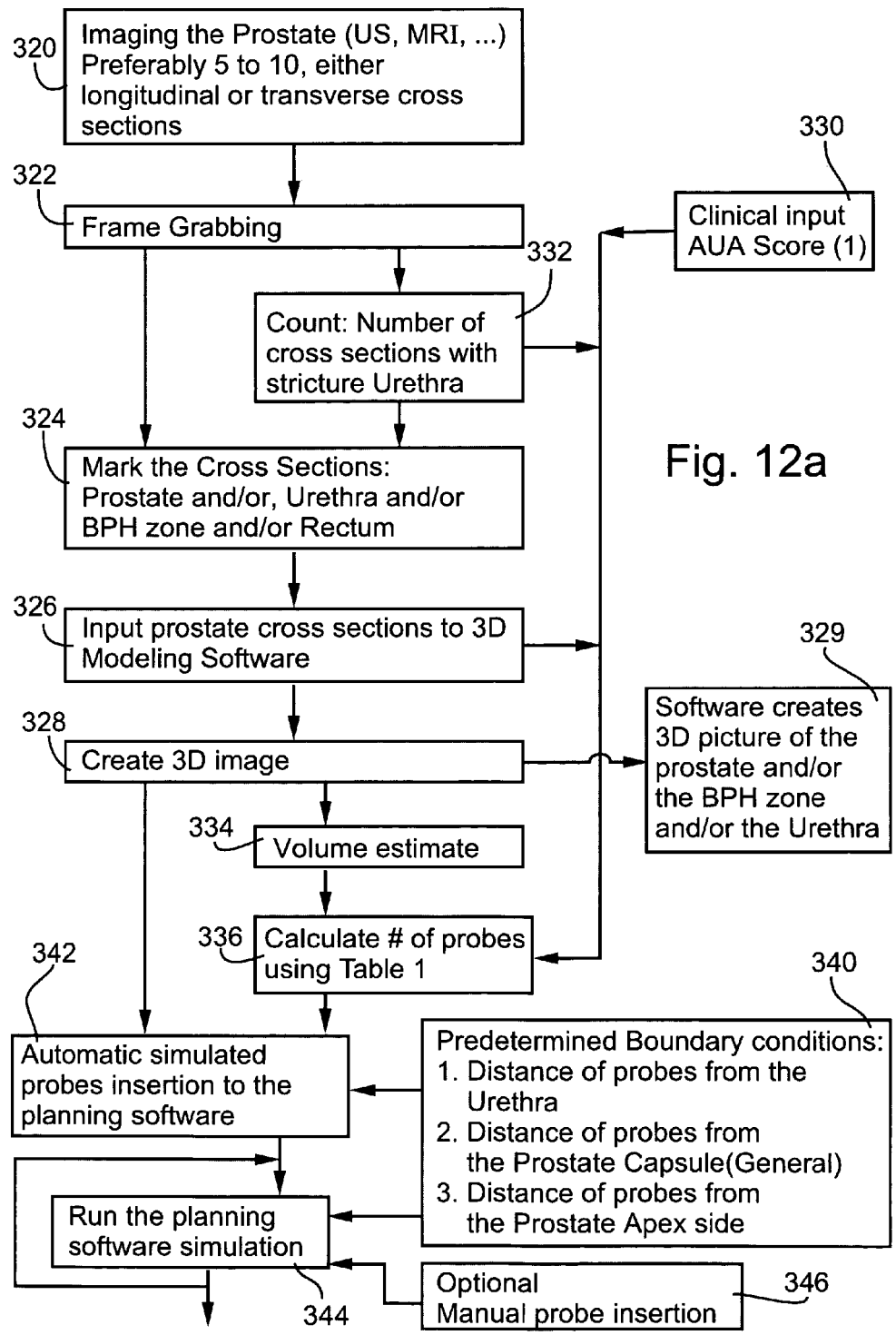
FIGS. 12a-12b are a flow chart showing a method for automatically generating a recommendation relating to a cryoablation procedure, according to an embodiment of the present invention.
Figure 12B:
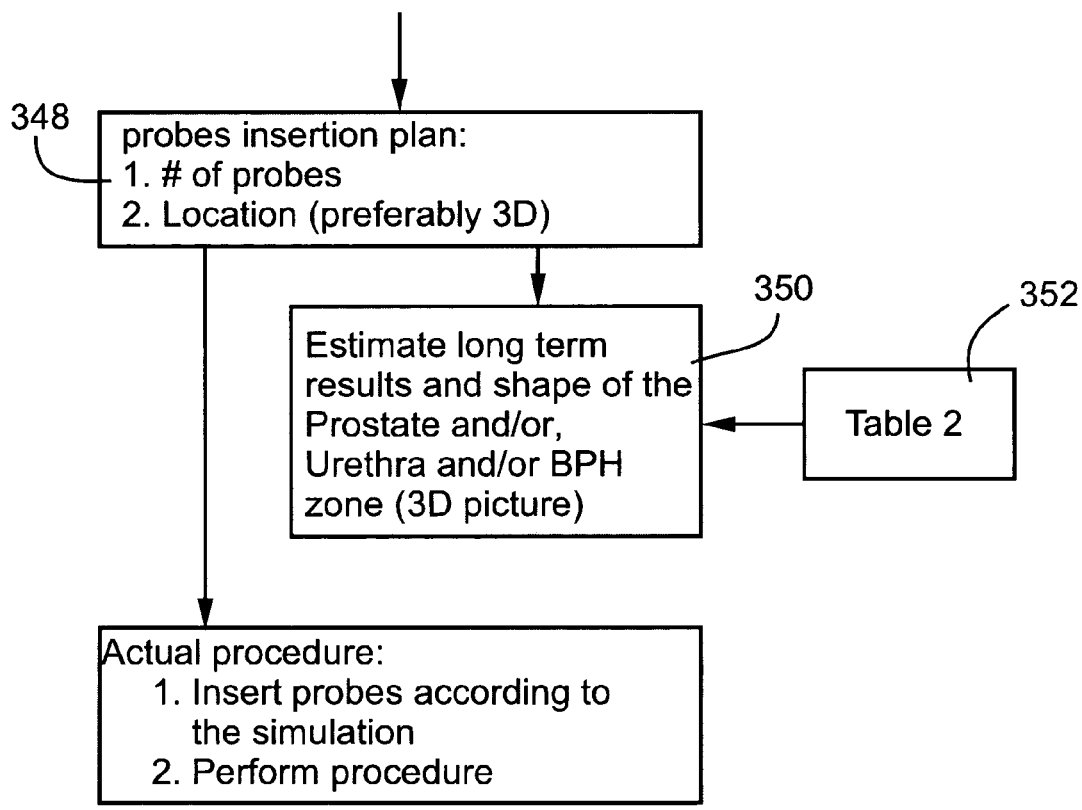

Reference is now made to FIGS. 12a and 12b, which is a flow chart showing a method for automatically generating a recommendation relating to a cryoablation procedure, utilizing the information of Table 2, or similar information, according to an embodiment of the present invention. In the specific example of FIGS. 12a-12b, the generated recommendation is relevant to cryoablation of tissues of a prostate for treatment of BPH.

At step 320 of FIG. 12a, first imaging modality 250 is used to create preparatory images, which are digitized at step 322 to become digitized preparatory images 254. In the example presented, images 254 are cross sections of a prostate such as those generated by a series of ultrasound scans taken at regularly intervals of progressive penetration into the body of a patient, as might be produced by the ultrasound equipment described with reference to FIGS. 8-10 hereinabove.

At optional step 324, an operator marks or otherwise indicates, with reference to images 254, locations of tissues to be cryoablated or to be protected, as explained hereinabove. At step 326 images 254 are input to three-dimensional modeler 256, which creates three-dimensional model 258 of the intervention site at step 328. Model 258, along with any operator-highlighted and classified regions of model 258, are displayed at step 329.

In a parallel process, raw materials for a recommendation are gathered. At step 330 clinical input in the form of an AUA score from a questionnaire of a patient's symptoms is input. At step 332 a count is made of the number of preparatory images 254 (cross-sections) of the urethra which show constriction to the urethra caused by pressure from the prostate tissue on the urethra. A count of cross-sections showing constriction is here taken as an indication of the length of a stricture. Determination of which cross-section images show signs of constriction may be made by an operator, or alternatively may be made by automated analysis of images 256, using image interpretation techniques well known in the art. At step 334, information available to three-dimension modeler 256 is used to automatically calculate the volume of the prostate.

At step 336, information assembled at steps 330, 332, and 334 is used in a table-lookup operation to retrieve a recommendation for the appropriate number of probes to be used to treat the imaged specific case of BPH.

At step 340, an operator optionally inputs specific boundary conditions which serve to limit recommendations by the system. Utilizing model 254 created at step 328, operator-specified boundary conditions from step 340, operator-specified identification of locations of specific tissues to be ablated or protected from step 324, and a calculated recommended number of probes from step 336, a recommendation for optimal positioning of a recommended number of probes may be made at step 342. Display of a recommended intervention is made at step 344.

Optionally, operator-specified placement of simulated cryoprobes may modify or replace the recommended intervention, at step 346.

Step 344 is optionally iterative. That is, an operator may repeatedly modify definitions of tissues, boundary conditions, or manual placement of simulated probes, until the operator is satisfied with the simulated results. As a part of step 344, activities of evaluator 300 may be evoked, so as to procure system feedback based on a simulated intervention. Step 344 is repeated so long as desired by an operator, and until the operator is satisfied with the results.

Referring now to FIG. 12b which is a continuation of the flowchart of FIG. 12a, at step 348 a final plan is optionally saved to a computer disk or other memory 270.

In optional step 350, details of the completed intervention plan can be used to estimate and display expected long-term results of the planned intervention, such as an expected future volume and shape of the prostate. Information from Table 2 or an equivalent is utilized for step 350, as indicated at step 352. It is noted that long-term volume of the prostate may also be treated as a boundary condition of an intervention, at step 340.

The example presented in FIGS. 12a and 12b refers specifically to a utilization of planning system 240 for treating a prostate for BPH. Similar utilizations may be contemplated, for treating other organs, or for treating other conditions of a prostate.

In treating BPH, a desired goal is a reduction in prostate volume so as to relieve pressure on the urethra of a patient, because pressure on the urethra from an enlarged prostate interferes with the process of urination. In treating BPH there is no need to destroy all of a selected volume, but rather simply to destroy some desired percentage of that volume.

In treating, for example, a prostate tumor suspected of malignancy, goals of the intervention are quite different. To avoid dangerous proliferation of malignant cells, it is desirable to ablate a defined volume in its entirety. In such a context, when it is necessity to destroy all tissues within a selected volume, the functionality of evaluator 300 of planning system 240 is particularly useful.

Evaluator 300 is able to calculate, for each arbitrarily selected small volume of model 258, the cumulative cooling effect of all cryoprobes in proximity to said selected small volume. Consequently evaluator 300 is able to make at least a theoretical determination of whether, for a given deployment of cryoprobes utilized under a given set of operating parameters, total destruction of malignant tissues within a selected volume is to be expected.

Figure 13:
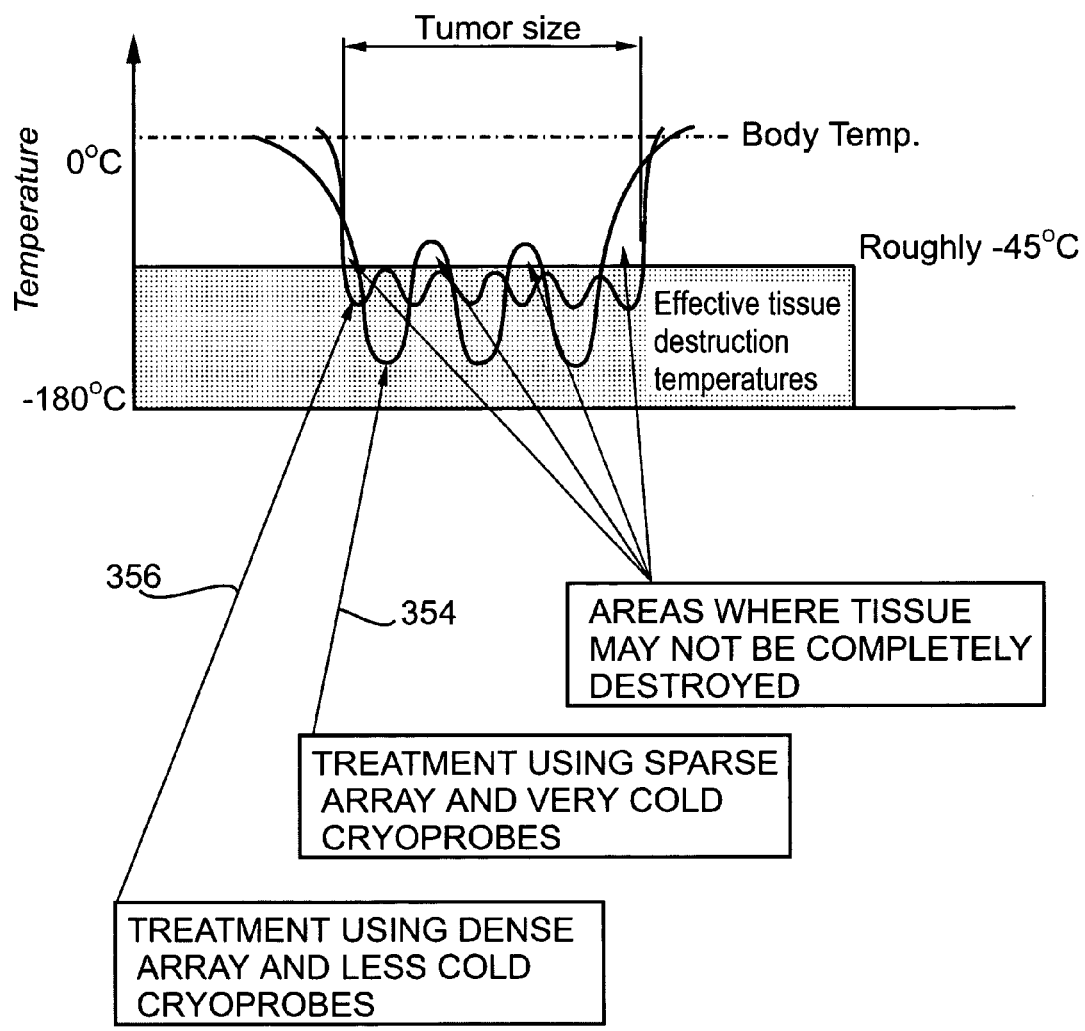
FIG. 13 is a chart showing temperature profiles for several cryoablation methods, is useful for understanding FIGS. 14 and 15.
Figure 14:
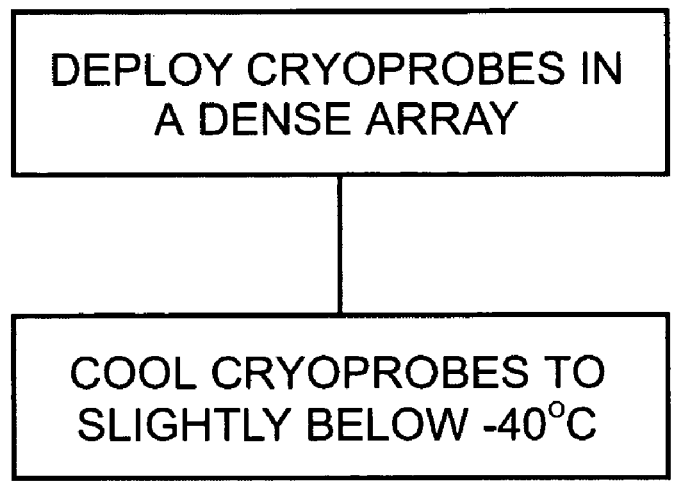
FIG. 14 is a simplified flow chart showing a method for ensuring total destruction of a selected volume while limiting damage to tissues outside that selected volume, according to an embodiment of the present invention.
Figure 15:
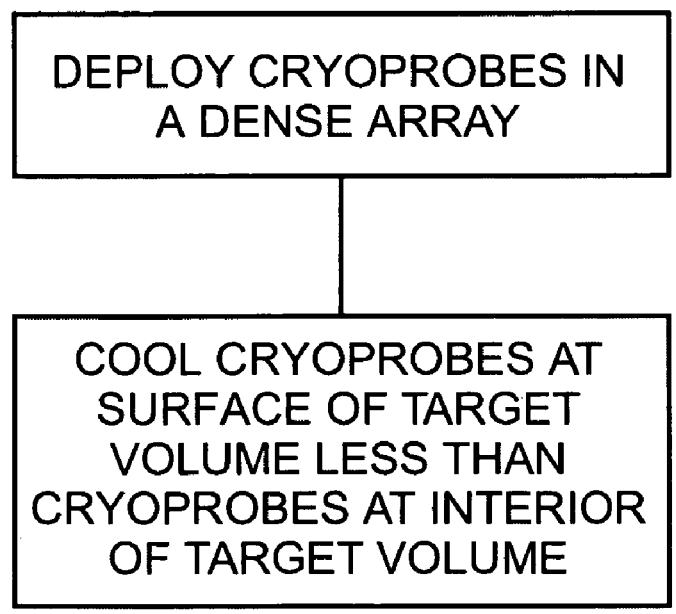
FIG. 15 is a simplified flow chart showing another method for ensuring total destruction of a selected volume while limiting damage to tissues outside that selected volume, according to an embodiment of the present invention.

Reference is now made to FIG. 13, which is a chart showing temperature profiles for several cryoablation methods, useful for understanding FIGS. 14 and 15. FIG. 13 contrasts the temperature profiles for cryoablation used in prior art systems 354 as compared to the temperature profiles 356 utilized according to the methods of FIGS. 14 and 15.

Reference is now made to FIG. 14, which is a simplified flow chart of a method for ensuring total destruction of a selected volume while limiting damage to tissues outside that selected volume, according to an embodiment of the present invention.

The method presented by FIG. 14 comprises (a) deploying a plurality of cryoprobes in a dense array within a target volume, and (b) limiting cooling of the deployed cryoprobes to a temperature only slightly below a temperature ensuring complete destruction of tissues. The temperature profile required is shown in detail in FIG. 13, where it is contrasted to a temperature profile according to methods of prior art. According to the method of FIG. 14, limiting cooling of each cryoprobe has the effect of limiting the destructive range of each cooled cryoprobe. If a plurality of cryoprobes are deployed in an sufficiently dense array and cooled to an extent such as that indicated in FIG. 13, a nearly-uniform cold field is created, the field being uniformly below a temperature required to ensure destruction of tissues within the field, yet there is relatively little tendency for destructive temperature to extend far beyond the deployed cryoprobe array. Thus, in contrast to methods of the prior art, the method presented by FIG. 14 relies on making a cryoprobe array more dense, and less cold. Control of degree of cooling may of course be accomplished by controlling a temperature of cryoprobes of the array, either individually or collectively, or by controlling duration of cooling of cryoprobes of the array, or both.

Reference is now made to FIG. 15, which is a simplified flow chart of another method for ensuring total destruction of a selected volume while limiting damage to tissues outside that selected volume, according to an embodiment of the present invention.

The method of FIG. 15 is similar to that of FIG. 14, in that it utilizes a dense array of cryoprobes cooled to a lesser extent than the cooling utilized according to methods of prior art.

According to the method of FIG. 15, however, cryoprobes at the periphery of a target volume are cooled less than are cryoprobes at the interior of the target volume. Cryoprobes at the interior of the target volume are, by definition, relatively distant from tissues desired to be protected, consequently they can be strongly cooled with impunity, thereby helping to ensure total destruction of target tissues. In contrast, cryoprobes near the surface of the target volume are closer to healthy tissues, consequently it is desirable to cool them less, so as to limit the damage they cause. Such lesser cooling of surface cryoprobes is possible, without sacrificing efficient destruction of target tissues, because a combination of weak cooling from surface probes together with strong cooling from interior probes creates a near-uniform cold field near the surface probes which ensures destruction of tissues on an interior side of the surface probes, while causing relatively little destruction of tissues on an exterior side of the surface probes.

Planning system 240 can be used effectively to plan dense arrays of cryoprobes according the methods of FIG. 14 and of FIG. 15. For example, a user might specify a particular density of an array of probes, then use evaluator 300 to evaluate a range of possible temperature and duration parameters to find an amount and duration of cooling which ensures that the specified array will indeed create a nearly-uniform cold field sufficient to destroy all target tissues. Alternatively, a user might specify a desired degree of cooling and use planning system 240 to recommend a required density of the cryoprobe array.

Thus, evaluator 300 and recommender 310 can be used to calculated placement and operational parameters of cryoprobes in a manner which guarantees a nearly-uniform cold field within a selected volume. If cryoprobes 266 are sufficiently small and placed sufficiently close together, cooling effects from a plurality of probes will influence each selected small volume within a target volume, and an amount of required cooling can be calculated which will ensure that all of the target volume is cooled down to a temperature ensuring total destruction of the target volume.

In implementing the method of FIG. 15, control of degree of cooling may of course be accomplished by controlling temperatures of cryoprobes of the array, either individually or collectively, or by controlling duration of cooling of cryoprobes of the array, or both.

Figure 16:
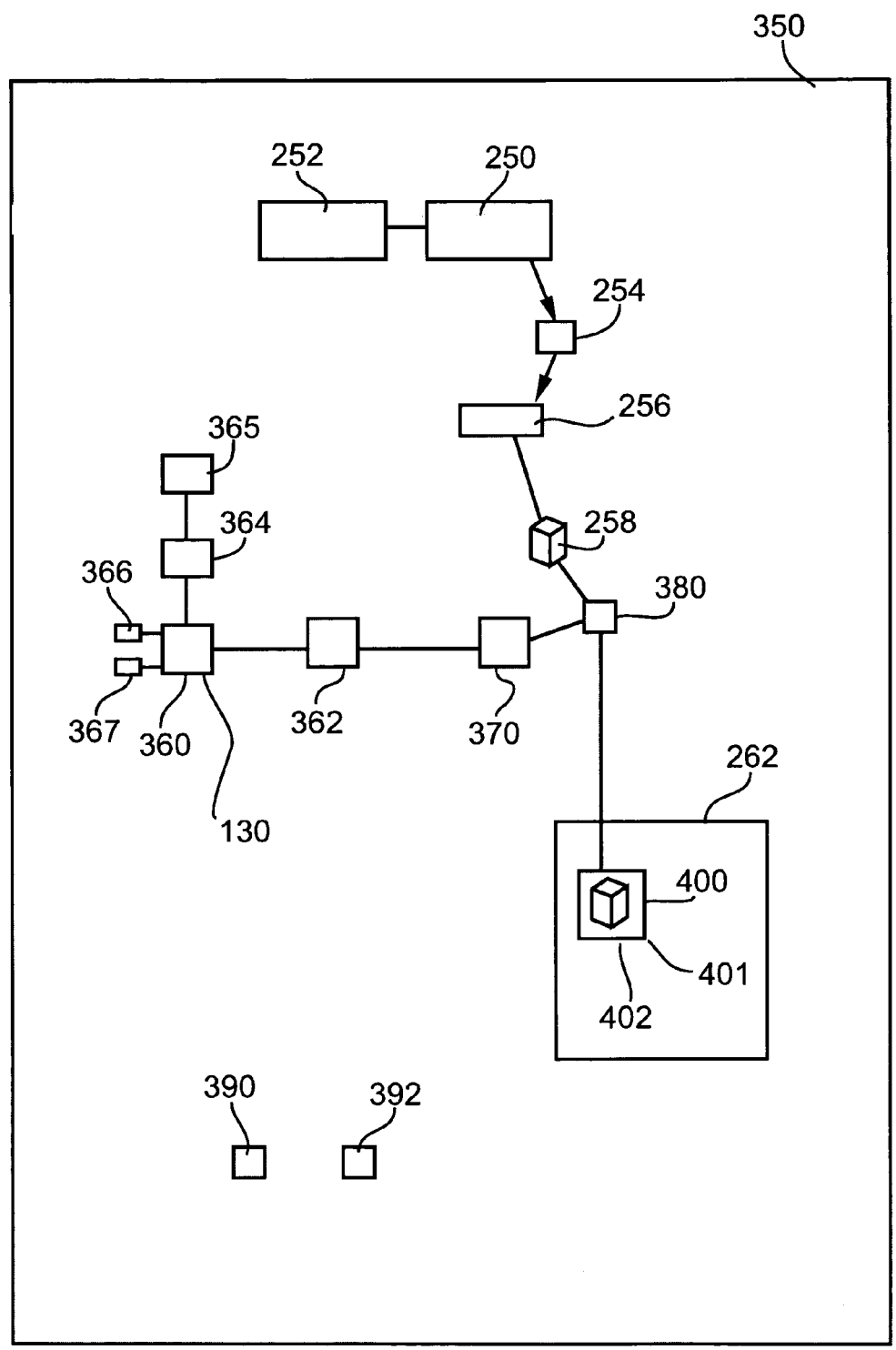
FIG. 16 is a simplified block diagram of surgical facilitation system for facilitating a cryosurgery ablation procedure, according to an embodiment of the present invention.

Reference is now made to FIG. 16, which is a simplified block diagram of a surgical facilitation system for facilitating a cryosurgery ablation procedure, according to an embodiment of the present invention.

In a preferred embodiment, a surgical facilitation system 350 comprises a first imaging modality 250 and optional digitizer 252, for creating digitized preparatory images 254 of an intervention site, a first three-dimensional modeler 256 for creating a first three-dimensional model 258 of the intervention site based on digitized preparatory images 254, a second imaging modality 360 with optional second digitizer 362 for creating a digitized real-time image 370 of at least a portion of the intervention site during a cryosurgery procedure, and an images integrator 380 for integrating information from three-dimensional model 258 of the site and from real-time image 370 of the site in a common coordinate system 390, thereby producing an integrated image 400 displayable by a display 260. Integrated image 400 may be a two dimensional image 401 created by abstracting information from a relevant plane of first three dimensional model 258 for combining with a real-time image 370 representing a view of that plane of that portion of the site in real-time. Alternatively, a set of real-time images 370 may be used by a second three dimensional modeler 375 to create a second three dimensional model 402, enabling images integrator 380 to express first three dimensional model 258 and second three dimensional model 402 in common coordinate system 390, preferably a Cartesian coordinate system, thereby combining both images into integrated image 400.

Various strategies may be used to facilitate combining of model 258 (based on preparatory images 254) with real-time images 370 (or model 402 based thereupon) by images integrator 380. Processes of scaling of images to a same scale, and of projection of a 'slice' of a three dimensional image to a chosen plane, are all well known in the art. Basic techniques for feature analysis of images are also well known, and can deal with problems of fine alignment of images from two sources, once common features or common directions have been identified in both images. Techniques useful for facilitating aligning of both images by images integrator 380 include: (a) identification of common features in both images by an operator, for example by identifying landmark features such as points of entrance of a urethra into, and points of exit of a urethra from, a prostate, (b) identification of constant basic directions, such as by assuring that a patient is in a similar position (e.g., on his back) during both preparatory imaging and real-time imaging, (c) operator-guided matching, through use of interface 264, of a first set of images, (d) use of proprioceptive tools for imaging, that is, tools capable of reporting, either mechanically or electronically using an electronic sensor 364 and digital reporting mechanism 365, their own positions and movements, and (e) using a same body of imaging equipment to effect both preparatory imaging, producing preparatory images 254, and real-time imaging during a cryosurgery procedure, producing real-time images 370. For example, using ultrasound probe 130 of FIGS. 8-10 and FIG. 16 both for preparatory imaging and for real-time imaging, and assuring that the patient is in a standard position during both imaging procedures, greatly facilitates the task of images integrator 380. Equipping ultrasound probe 130 with stabilizer 366 and controlling its movements with stepper motor 367, as shown in FIG. 16, yet further simplifies the task of images integrator 380.

It will be appreciated that the present invention can benefit from position tracking of various components thereof so as to assist either in modeling and/or in actually controlling a cryoablation procedure. Position tracking systems per se are well known in the art and may use any one of a plurality of approaches for the determination of position in a two- or three-dimensional space as is defined by a system-of-coordinates in two, three and up to six degrees-of-freedom. Some position tracking systems employ movable physical connections and appropriate movement monitoring devices (e.g., potentiometers) to keep track of positional changes. Thus, such systems, once zeroed, keep track of position changes to thereby determine actual positions at all times. One example for such a position tracking system is an articulated arm. Other position tracking systems can be attached directly to an object in order to monitor its position in space. An example of such a position tracking system is an assortment of three triaxially (e.g., co-orthogonally) oriented accelerometers which may be used to monitor the positional changes of the object with respect to a space. A pair of such assortments can be used to determine the position of the object in six-degrees of freedom.

Other position tracking systems re-determine a position irrespective of previous positions, to keep track of positional changes. Such systems typically employ an array of receivers/ transmitters which are spread in known positions in a three-dimensional space and transmitter(s)/receiver(s), respectively, which are in physical connection with the object whose position being monitored. Time based triangulation and/or phase shift triangulation are used in such cases to periodically determine the position of the monitored object. Examples of such a position tracking systems employed in a variety of contexts using acoustic (e.g., ultrasound) electromagnetic radiation (e.g., infrared, radio frequency) or magnetic field and optical decoding are disclosed in, for example, U.S. Pat. Nos. 5,412,619; 6,083,170; 6,063,022; 5,954,665; 5,840,025; 5,718,241; 5,713,946; 5,694,945; 5,568,809; 5,546,951; 5,480,422 and 5,391,199, which are incorporated by reference as if fully set forth herein.

Position tracking of any of the imaging modalities described herein and/or other system components, such as the cryoprobes themselves, and/or the patient, can be employed to facilitate implementation of the present invention.

In a preferred embodiment, surgical facilitation system 350 further comprises all functional units of planning system 240 as described hereinabove. That is, facilitation system 350 optionally comprises simulator 260 having user interface 264 with highlighter 280, each having parts, functions and capabilities as ascribed to them hereinabove with reference to FIG. 11 and elsewhere. In particular, system 350 includes the above-described interface useable by an operator to specify placements and operational parameters of simulated cryoprobes 266, and to specify tissues to be cryoablated or to be protected during cryoablation.

Similarly, facilitation system 350 further optionally comprises memory 270, predictor 290, evaluator 300, and recommender 310, each having parts, functions and capabilities as ascribed to them hereinabove with reference to FIG. 11 and elsewhere.

Thus, in a preferred embodiment of the present invention, facilitation system 350 is able to undertake all activities described hereinabove with respect to planning system 240. In addition, facilitation system 350 is able to provide a variety of additional services in displaying and evaluating at least one real-time image 370, and is further able to compare real-time images 370 to three dimensional model 258, and also to compare information from real-time images 370 to stored information such as that identifying operator-specified tissues to be cryoablated or to be protected, as is explained more fully hereinbelow.

In a preferred embodiment, either first imaging modality 250 and/or second imaging modality 360 may each independently be a magnetic resonance imaging system (MRI), an ultrasound imaging system, a computerized tomography imaging system (CT), some combination of these systems, or some similar system able to produce images of the internal tissues and structures of the body of a patient, yet in the case of second imaging modality 360, ultrasound and MRI imaging are more typically used, as being more conveniently combined with cryosurgery processes.

Facilitation system 350 further comprises a first comparator 390, for comparing first three-dimensional model 248 with real-time image 370, particularly to discern differences between both images. Such differences constitute differences between a status of a planned intervention and a status of an actual intervention in real-time. Tools, such as cryoprobes, tissues, such as a urethra, and ice-balls formed during cryoablation, all figure as elements in three dimensional model 258, and all may be visualized using second imaging modality 360. Thus, their expected positions, sizes, orientations, and behaviors may be compared to their actual real-time positions, sizes, orientations and behaviors during cryoablation, by comparator 390.

Differences thereby revealed, and information concerning such differences, can be of vital importance to an operator in guiding his actions during an intervention, particularly if the operator deviates from a planned intervention without being aware of doing so. A representation of the revealed differences may be displayed by displayer 262 and highlighted for greater visibility. A feedback mechanism 392, for example an auditory feedback mechanism, may be used to draw attention of an operator to serious discrepancies between a planned and an actual intervention.

Similarly, comparator 390 can be used to compare status of objects visible in real-time images 370 with stored information about operator-specified tissues to be cryoablated. Comparator 390 can thus provide information about, and displayer 262 can display, situations in which tissues intended to be cryoablated are in fact not effectively being cryoablated by a procedure. Similarly, comparator 390 can be used to check status of objects visible in real-time images 370, relating them to stored information about operator-specified tissues which are to be protected during cryoablation. In the case of discrepancies between an actual situation and an operator-specified desirable situation, display 262 and feedback mechanism 392 can warn an operator when a procedure seems to be endangering such tissues.

The capabilities of facilitation system 350 may extend yet further, to direct guidance to an operator in the manipulation of cryoablation tools, and even to partial or complete control of such tools during a phase of a cryoablation intervention.

Figure 17:
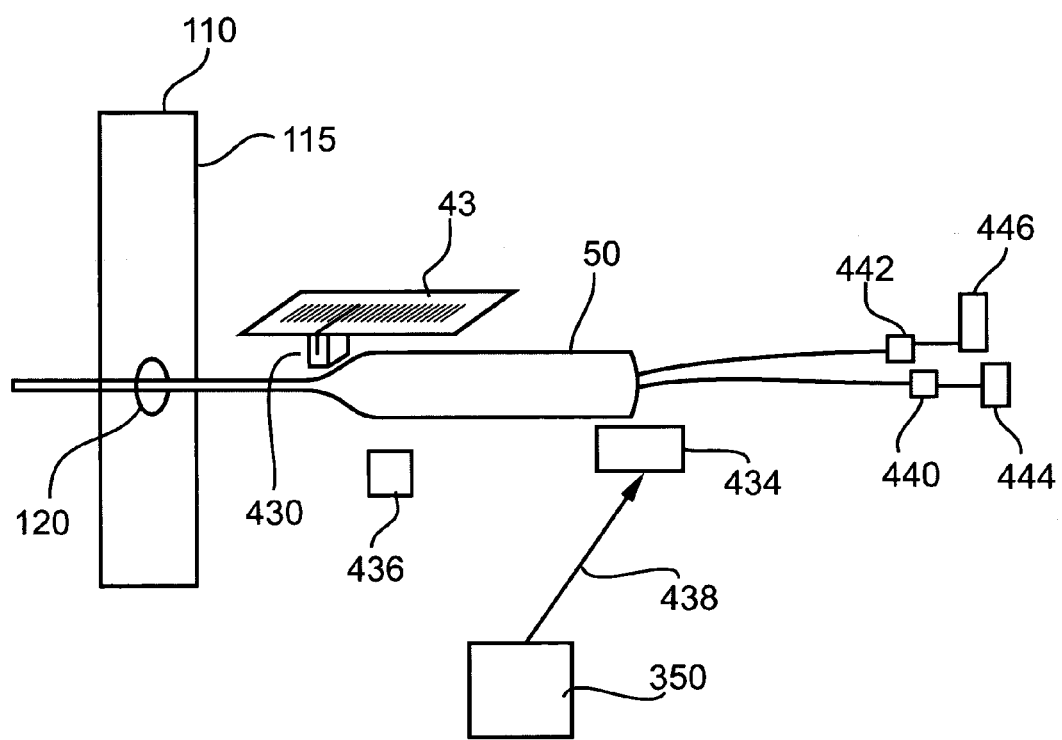
FIG. 17 is a schematic diagram of mechanisms for control of cryosurgical tools by a surgical facilitation system, according to an embodiment of the present invention.

Reference is now made to FIG. 17, which is a schematic diagram of mechanisms for control of cryosurgical tools by a surgical facilitation system, according to an embodiment of the present invention.

A cryosurgical probe 50 is shown passing through an aperture 120 in a guiding element 115 which is realized in this example as a plate 110. As described hereinabove in the context of the discussion of FIGS. 8-10, aperture 120 is for limiting sideways movement of probe 50, which is however free to move forward and backwards towards and away from a cryoablation site in a patient. In the prior art methods presented in FIGS. 8-10, such movement was conceived as under sole and exclusive control of an operator who advanced and retracted probe 50 manually.

As has been noted above, the simulation, evaluation, and recommendation capacities of planning system 240 and facilitation system 350, based on preparatory images 254 and three dimensional model 258, allow system 350 to calculate a recommended maximum and minimum depth for at which each cryoprobe 50 is to be used for cryoablation. Further, a cryoablation plan manually entered by an operator may also determine a maximum and minimum depth at which each cryoprobe 50 is to be used for cryoablation.

In a simple implementation of mechanical control based on information from planning system 240 or facilitation system 350, planned maximum and minimum depths generated by those systems are communicated to an operator who adjusts a mechanical blocking element 430 according to a graduated distance scale 432, in a manner which limits forward or backward movement of probe 50 so as to prevent an operator from unintentionally and unknowingly advancing or retracting probe 50 beyond limits of movement planned for probe 50. Such an arrangement guides and aids an operator in use and control of probe 50 for effecting cryoablation according to a plan.

In a somewhat more sophisticated implementation, control signals 438 from system 350 activate a stepper motor 434 to directly control movement of probe 50. Thus, under control of system 350 and according to a planned, simulated, examined and theoretically tested procedure, stepper motor 434 can advance probe 50 to a planned depth for performing cryoablation. System 350 can also send temperature control signals to heating gas valve 440 and cooling gas valve 442, thereby controlling a flow of heating gas from heating gas reservoir 444 and a flow of cooling gas from s cooling gas reservoir 446. Thus, under control of an intervention plan and utilizing mechanisms presented in FIG. 17, system 350 is able to directly control some or all of a cryoablation intervention. Thus, in a typical portion of a cryoablation procedure, stepper 434 advances probe 50 a planned distance, cooling gas valve 442 opens to allow passage of a gas which cools probe 50 to cryoablation temperatures and maintains those temperatures for a planned length of time, then cooling valve 442 closes to halt cooling. Optionally, heating gas valve 440 then opens to allow passage of a gas which heats probe 50 so as to melt tissues in contact with probe 50, thereby restoring to it freedom of motion, whereupon stepper motor 434 can further advance or retract probe 50 to a new cryoablation position, at which new position system 350 can optionally repeat this cryoablation process.

To ensure accuracy, movement of cryoprobe 50 may be monitored by a movement sensor 436. Moreover, all the facilities of system 350 previously described, for comparing real-time positions of objects with planned positions of those objects, can be brought to bear, to monitor this independently controlled cryoablation process.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for planning a cryosurgical ablation procedure, comprising:
   (a) utilizing a first imaging modality to create digitized preparatory images of an intervention site;
   (b) utilizing a three-dimensional modeler to create a three-dimensional model of said intervention site based on said digitized preparatory images;
   (c) utilizing a simulator to simulate a cryosurgical intervention, which simulator comprises a displayer operable to display in a common virtual space an integrated image comprising a visualization of said three-dimensional model of said intervention site and a virtual display of at least one simulated cryoprobe inserted at least one selected locus;
   (d) utilizing a predictor to predict an effect on body tissues of a patient of operation of said at least one cryoprobe at said at least one selected locus according to selected operational parameters, said predictor being operable to predict size and shape of a prostate two or more weeks after said operation of said at least one cryoprobe, thereby enabling to plan said cryoablation procedure in view of said predicted effect;
   (e) utilizing a recommender to recommend a preference among a plurality of operating schema, wherein each schema presents one or more user-designated plans for placement and operation of said at least one cryoprobe.

2. The method of claim 1, further comprising displaying, in said integrated image, a visualization of an effect predicted by said predictor.

3. The method of claim 1, wherein said simulator further comprises an interface useable by an operator for specifying at least one operator-specified locus for insertion of said at least one simulated cryoprobe.

4. The method of claim 1, wherein said simulator further comprises an interface useable by an operator for specifying operator-specified parameters for operation of said at least one simulated cryoprobe.

5. The method of claim 1, wherein said simulator further comprises a second recommender operable to recommend a position for inserting a cryoprobe into a body of a patient.

6. The method of claim 1, wherein said simulator further comprises a second recommender for recommending operating parameters for a cryoprobe inserted in a body of a patient.

7. The method of claim 1, further comprising using said predictor to predictor size and position of an iceball created by operation of said at least one simulated cryoprobe.

8. The method of claim 1, further comprising using said predictor to predict size and position of an iceball created by operation of said at least one simulated cryoprobe.

9. The method of claim 1, further comprising using a second recommender to recommend temperature and duration for cooling of said at least one simulated cryoprobe.

* * * * *